United States Patent [19]

Matsumoto et al.

[11] Patent Number: 5,418,230

[45] Date of Patent: May 23, 1995

[54] BENZYLIDENE DERIVATIVES

[75] Inventors: Saichi Matsumoto, Ikeda; Tatsuo Tsuri, Kobe; Masanao Inagaki, Osaka; Hirokuni Jyoyama, Nara, all of Japan

[73] Assignee: Shionogi & Co., Ltd., Osaka, Japan

[21] Appl. No.: 142,146

[22] Filed: Oct. 28, 1993

[30] Foreign Application Priority Data

Oct. 28, 1992 [JP] Japan .................. 4-289972

[51] Int. Cl.$^6$ ............ C03D 275/02; A61K 31/54
[52] U.S. Cl. ............... 514/222.2; 514/222.5; 514/342; 514/372; 514/446; 544/2; 544/3; 546/280; 548/214; 549/78
[58] Field of Search ............ 548/214; 549/78; 544/2, 544/3; 546/280; 514/372, 446, 222.2, 222.5, 342

[56] References Cited

U.S. PATENT DOCUMENTS 4,895,862  1/1990  Alessi .................................. 514/360

FOREIGN PATENT DOCUMENTS 0204964 12/1986 European Pat. Off. .
0211670  2/1987 European Pat. Off. .
0334119  9/1989 European Pat. Off. .
0371438  6/1990 European Pat. Off. .
0525197  2/1993 European Pat. Off. .

OTHER PUBLICATIONS

Mueller et al., Chemical Abstracts, vol. 117 (1992), p. 736 Abstract No. 131100q.
Speranskii, C.A. 84(1)4761F (1975).

*Primary Examiner*—Robert Gerstl
*Attorney, Agent, or Firm*—Wenderoth, Lind & Ponack

[57] ABSTRACT

Benzylidene derivatives having anti-inflammatory activities, are shown by the following formula I:

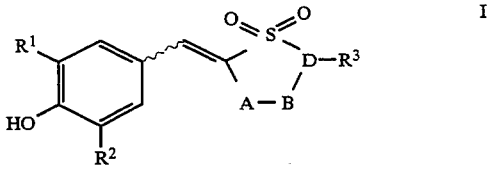

wherein A is -CH$_2$- or -CH$_2$CH$_2$-; B is a bond or -CH$_2$-, -CHOH-, -CO-, -O-, or A and B may taken together form -CH=CH-; D is >N- or >CH-; R$^1$ and R$^2$ each independently is hydrogen, lower alkyl or lower alkoxy; R$^3$ is hydrogen, lower alkyl, cycloalkyl, lower alkoxy, arylalkyloxy, heteroarylalkyloxy, lower alkylcarbonyl, arylcarbonyl, substituted or unsubstituted carbamoyl, or a group of the formula:

-(CH$_2$)$_n$-R$^4$ wherein R$^4$ is hydrogen, hydroxy, substituted or unsubstituted amino, aryl, heteroaryl, hydroxycarbonyl or lower alkyloxycarbonyl; n is an integer of 0-3.

6 Claims, No Drawings

BENZYLIDENE DERIVATIVES

FIELD OF THE INVENTION

The present invention relates to novel benzylidene derivatives which have anti-inflammatory activities.

BACKGROUND OF THE INVETION

Nonsteroidal anti-inflammatory drugs such as lysozyme chloride and the like have been effective for the amelioration of initial symptoms and acute inflammations of rheumatism but ineffective for the improvement of progressed conditions of chronic rheumatism with bone destructions, or for the treatment of bone osteoarthritis and the like. Further, the conventional drugs might cause gastric ulcer because of their strong actions.

Recently, it has become apparent that leukotrienes (LT), especially $LTB_4$ and the like, which are metabolic products in the metabolic pathway of arachidonic acid with 5-lipoxygenase, are important mediators of inflammatory reactions. It is also suggested that interleukin-1 (IL-1) being one type of cytokines is responsible for inflammation, greatly for chronic rheumatism in particular. Under the conditions above, it has been considered that the compounds which inhibit the production of both $LTB_4$ and IL-1 are promising as antiinflammatory drugs. Such compounds are more useful than conventional nonsteroidal anti-inflammatory drugs because they are expected to be effective on not only acute inflammations but also chronic inflammations such as chronic rheumatism and the like.

Various compounds useful as anti-inflammatory drugs have been disclosed in Japanese patent Publication (KOKAI) Nos. 79944/1983, 257962/1986, 42977/1987, 305028/1989, 4729/1990, 256645/1990, 270865/1990, Japanese patent WO 89/503782 and the like. To obtain compounds which are effective for the treatment of chronic inflammations with lower side-effects such as gastric disorders, it has been continuously demanded to develop compounds which can efficiently suppress the production of mediators of inflammations such as prostaglandin $E_2$ ($PGE_2$), $LTB_4$, IL-1 and the like.

The present inventors have found that a certain kind of benzylidene derivatives remarkably inhibit the production of $PGE_2$, as well as that of cytokines such as $LTB_4$, IL-1 and the like, and have accomplished the present invention.

DESCRIPTION OF THE INVENTION

Thus, the present invention provides a compound of the formula I:

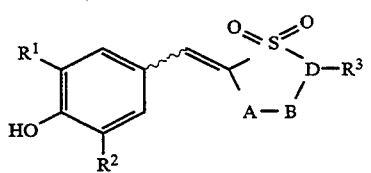

wherein A is $-CH_2-$ or $-CH_2CH_2-$; B is a bond or $-CH_2-$, $-CHOH-$, $-CO-$, $-O-$, or A and B may taken together form $-CH=CH-$; D is $>N-$ or $>CH-$; $R^1$ and $R^2$ each independently is hydrogen, lower alkyl or lower alkoxy; $R^3$ is hydrogen, lower alkyl, cycloalkyl, lower alkoxy, arylalkyloxy, heteroarylalkyloxy, lower alkylcarbonyl, arylcarbonyl, substituted or unsubstituted carbamoyl, or a group of the formula:

$-(CH_2)_n-R^4$ wherein $R^4$ is hydrogen, hydrgxy, substituted or unsubstituted amino, aryl, heteroaryl, hydroxycarbonyl or lower alkyloxycarbonyl; and n is an integer of 0-3.

Typical compounds of the formula I include those wherein the sulfur-containing heterocyclic ring in the formula I is shown by the following formulas.

 (a)

 (b)

 (c)

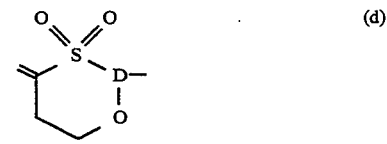 (d)

 (e)

 (f)

Wherein D is $>N-$ or $>CH-$.

Preferred compounds of the formula I include those wherein the sulfur-containing heterocyclic ring in the formula I is shown by the following formulas.

 (a-1)

 (a-2)

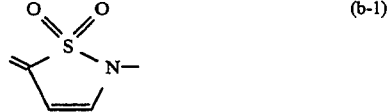 (b-1)

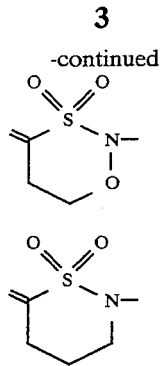

(d-1)

(e-1)

As is apparent from the above formula, compound I can be present in the stereostructures of both (E)-and (Z)-type. Accordingly, the compound I described in this specification should include both (E)- and (Z)-isomers unless otherwise noted.

For purposes of the present invention, as disclosed and claimed herein, the following terms are defined as below.

The term "lower alkyl" means straight or branched chain $C_1$-$C_8$ alkyl including methyl, ethyl, n-propyl, i-propyl n-butyl, i-butyl, s-butyl, t-butyl, n-pentyl, i-pentyl, neopentyl, s-pentyl, t-pentyl, n-hexyl, neohexyl, i-hexyl, s-hexyl, t-hexyl, heptyl and octyl. Preferable lower alkyl group is a straight or branched chain $C_1$-$C_4$ alkyl and the most preferable-one is methyl or ethyl.

The term "lower alkoxy" means straight or branched chain alkyloxy of 1 to 6 carbon atoms and includes methoxy, ethoxy, n-propoxy, i-propoxy, n-butoxy, i-butoxy, s-butoxy, t-butoxy, n-pentyloxy, i-pentyloxy, neopentyloxy, s-pentyloxy, t-pentyloxy, n-hexyloxy, neohexyloxy, i-hexyloxy, s-hexyloxy and t-hexyloxy. Preferable lower alkoxy group is a $C_1$-$C_3$ alkoxy group and the most preferable one is methoxy.

The term "cycloalkyl" means cycloalkyl of 3 to 7 carbon atoms and includes cyclopropyl, cyclobutyl, cyclopentyl, cyclohexyl and cycloheptyl. $C_3$ –$C_5$ cycloalkyl is particularly preferred.

The term "aryl" means substituted or unsubstituted phenyl or naphthyl. The aryl may be substituted by one or more substituents selected from halogen, lower alkoxy, lower alkyl and nitro. Examples of aryl include phenyl,4-chlorophenyl,4-methoxyphenyl,4-nitrophenyl, 3,4-dichlorophenyl,3,4-dimethoxyphenyl,3,4-dinitrophenyl, 1-naphtyl and 2-naphtyl.

The term "arylalkyloxy" means a group formed by substituting an aryl group(s) on to an alkoxy group as defined above. Examples of arylalkyloxy include benzyloxy,4-chlorobenzyloxy, 4-methoxybenzyloxy,3,4-dichlorobenzyloxy, 3,4-dimethoxybenzyloxy,4-nitrobenzyloxy,2-phenylethyloxy, 2-(4-chlorophenyl)ethyloxy,2-(4-methoxyphenyl)ethyloxy,1naphtylmethyloxy and 2-naphtylmethyloxy. The most preferred one is benzyloxy.

The term "heteroaryl" means a cyclic group containing 1–4 hetero atoms. Examples include pyridyl, thiazolyl, isothiazolyl, oxazolyl, isoxazolyl, imidazolyl, triazolyl and tetrazolyl. For purposes of the present invention, pyridyl, thiazolyl, oxazolyl and imidazolyl are preferred and pyridyl is most preferred.

The term "heteroarylalkyloxy" means a group formed by substituting a heteroaryl group(s) on to an alkoxy group as defined above. Examples include 2-pyridylmethyloxy, 3-pyridylmethyloxy,4-pyridylmethyloxy, 2-imidazolylmethyloxy,4-imidazolylmethyloxy,2-thiazolylmethyloxy and 4-thiazolylmethyloxy.

Examples of "lower alkylcarbonyl" include acetyl, propionyl, butyryl, valeroyl, hexanoyl, heptanoyl and octanoyl.

Examples of "arylcarbonyl" include benzoyl,4-chlorobenzoyl, 4-methoxybenzoyl,4-nitrobenzoyl,3,4-dichlorobenzoyl, 3,4-dimethoxybenzoyl,3,4-dinitrobenzoyl, 1-naphthoyl and 2-naphthoyl.

The term "substituted or un-substituted carbamoyl" means carbamoyl groups optionally substituted at the nitrogen atom by any one or more substitutents selected from lower alkyl, lower alkoxy, hydroxy, cycloalkyl, arylalkyl, alkoxyalkyl, alkylcarbonyl, arylcarbonyl, cycloalkyloxy and arylalkyloxy. Preferred substituents are lower alkyl, lower alkoxy and hydroxy. Examples of substituted carbamoyl include N-methylcarbamoyl, N,N-dimethylcarbamoyl, N-hydroxycarbamoyl, N-methyl-N-hydroxycarbamoyl, N-methoxycarbamoyl, N-methoxy-N-methylcarbamoyl, N-ethylcarbamoyl, N,N-diethylcarbamoyl, N-ethyl-N-hydroxycarbamoyl, N-propylcarbamoyl, N,N-dipropylcarbamoyl and N-propyl-N-hydroxycarbamoyl.

The term "halogen" means fluorine, chlorine, bromine and iodine.

Examples of "lower alkyloxycarbonyl" include methoxycarbonyl, ethoxycarbonyl, propoxycarbonyl, isopropoxycarbonyl, butoxycarbonyl, isobutoxycarbonyl and tert-butoxycarbonyl.

The term "substituted amino" means mono— or di-substituted amino and substituents are selected from lower alkyl and arylalkyl as defined above.

The compounds of the present invention have shown excellent in vitro activities in the suppression of the production of $PGE_2$, $LTB_4$ and IL-1 compared to E5110 and indomethacin which are used as control compounds as described in the following Experimental Examples. Further, it has been proved in vivo that the compounds I suppress edema with only a little damages of gastric mucosa, demonstrating that they can be excellent nonsteroidal anti-inflammatory agents.

The benzylidene derivatives of the present inventions are novel and can be prepared, for example, by methods described in (1) to (4) below. However, the present invention is by no means limited to those prepared by these methods and includes all the compounds I prepared by any other known methods.

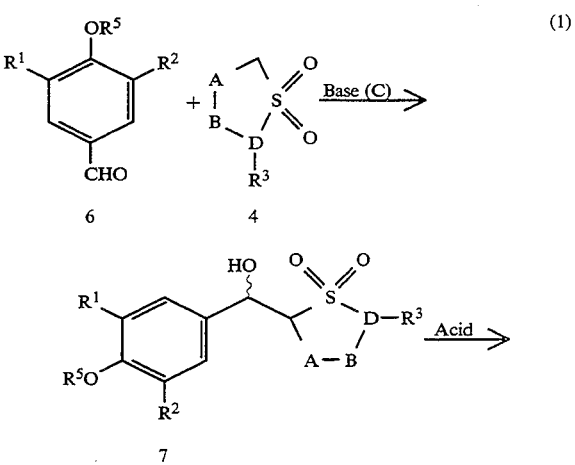

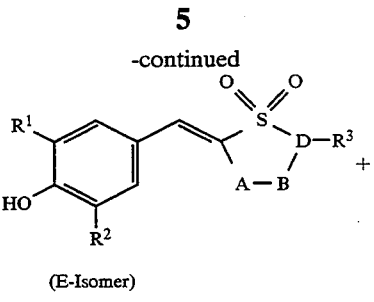

(E-Isomer)
8

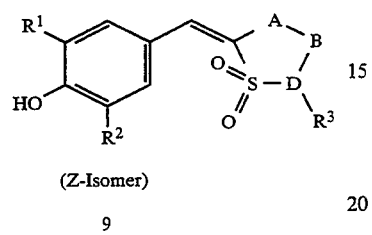

(Z-Isomer)
9

Wherein A, B, D, $R^1$, $R^2$, and $R^3$ are as defined above and $R^3$ is hydrogen or a hydroxy-protecting group.

One of the starting compounds, the sulfur-containing compound 4 can be prepared, for example, according to a reaction scheme below.

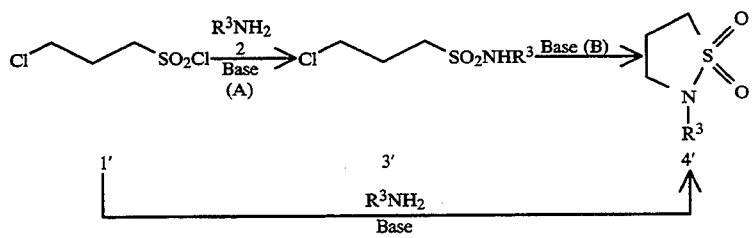

Wherein R3 is as defined above.

3-Chloropropylsulfonyl chloride 1' is reacted with amine 2 to yield sulfonamide intermediate 3'.

The reaction is carried out in the presence of base (A), if necessary, in a solvent selected from ether, chloroform, methylene chloride, dichloromethane, dichloroethane, tetrahydrofuran, dimethoxyethane, diethoxyethane, benzene, toluene, xylene, ethyl acetate, methyl acetate and the like, which solvent may contain water. The amine ($R^3NH_2$) may be a hydrochloride The base (A) used in case of necessity includes alkali metal bases such as lithium hydroxide, sodium hydroxide, potassium hydroxide, sodium carbonate, potassium carbonate, sodium hydrogencarbonate and potassium hydrogencarbonate and the like, and organic bases such as pyridine,4-N,N-dimethylaminopyridine (DMAP), triethylamine, diisobutyl ethylamine,1,8-diazabicyclo[5,4,o]undec-7-ene (DBU),1,4diazabicyclo[2,2,2] octane (DABCO) and the like. When an alkali metal base is used, it is preferable to add a phase transfer catalyst, if necessary. Examples of preferred phase transfer catalysts are quaternary ammonium salts such as N-benzyltrimethylammonium salts, tetrabutylammonium salts and the like.

The reaction where sulfonamide intermediate 3' is converted into sulfur-containing compound 4' can be carried out in the presence of a base (B) in a solvent selected from those described above. Anhydrous solvents such as dimethyl sulfoxide, dimethylformamide and the like are preferable. Sodium hydride and lithium-hydride can be used as base B as well as those described above.

Alternatively, sulfur-containing compound 4' can be prepared at once from compound 1' without separation of sulfonamide intermediate 3'. In this case, the reaction of compound 1' with amine 2 is carried out in a suitable solvent in the presence of two equivalents of a base. The solvent and the base may be selected from those exemplified above but it is particularly preferable to use sodium hydride as a base and dimethylformamide as a solvent.

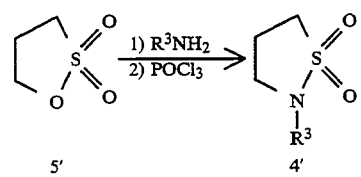

5'    4'

Alternatively, the desired sulfur-containing compound 4' can be also obtained from commercially available γ-sultone 5'. (See Reference Examples.) Namely, compound 5' is allowed to react with amine ($R^3NH_2$) and the resultant product is treated with a dehydrating agent. The reaction can be carried out without solvent but may be conducted in a solvent described above, if necessary. Examples of dehydrating agent usable include those commonly used such as phosphorus oxychloride, thionyl chloride, phosphorus pentachloride, phosphorus pentoxide and the like with a preference for phosphorus oxychloride.

The $R^5$ in compound 6 represents a hydrogen or a hydroxyl-protecting group. Hydroxyl-protecting groups include methoxymethyl, methoxyethoxymethyl, trimethylsilyl and tert-butyldimethylsilyl. Preferably, $R^5$ is a hydroxylprotecting group, in particular a methoxymethyl group.

The aldol reaction between compounds 6 and 4 obtained previously is carried out in the presence of a base (C) in a suitable solvent. Examples of base (C) include organic lithium salts such as n-butyllithium, secbutyllithium, tert-butyllithium, phenyllithium, lithium diisopropylamide, lithium diethylamide, lithium hexamethyldisilazane and the like, and alkali metal bases such as sodium hydride and potassium tert-butoxide and the like. Particularly, lithium diisopropylamide or lithium hexamethyldisilazane is preferable.

Examples of reaction solvents include ether solvents such as diethyl ether, tetrahydrofuran, dimethoxyethane, diethoxyethane and the like or hydrocarbon solvents such as n-hexane, cyclohexane and the like. The reaction is preferably conducted in the presence of a reagent that serves as a ligand of lithium metal, for example tetramethylethylenediamine, hexamethylphosphoramide and the like, if necessary.

The reaction is carried out at temperature ranging from −80° C. to +50° C. with preference in lower range.

Aldol addition compound 7 is converted to a mixture of compounds 8 and 9 in the presence of an acid. Examples of acids include organic acids such as trifluoroacetic acid, p-toluenesulfonic acid, camphorsulfonic acid and the like and inorganic acids such as sulfuric acid, hydrochloric acid and the like. Further, ordinary dehydrating agents such as thionyl chloride, methanesulfonyl chloride, alminium chloride, phosphorus oxychloride, phosphorus pentachloride and the like can be used. Preferably, the reaction is carried out with heating in an aromatic hydrocarbon such as benzene, toluene, xylene and the like, a halogenated hydrocarbon such as chloroform, dichloromethane, dichloroethane and the like, or an ether solvent such as tetrahydrofuran, dimethoxyethane, diethoxyethane and the like.

and 10b of the formula I wherein D is >N- and $R^3$ is H.

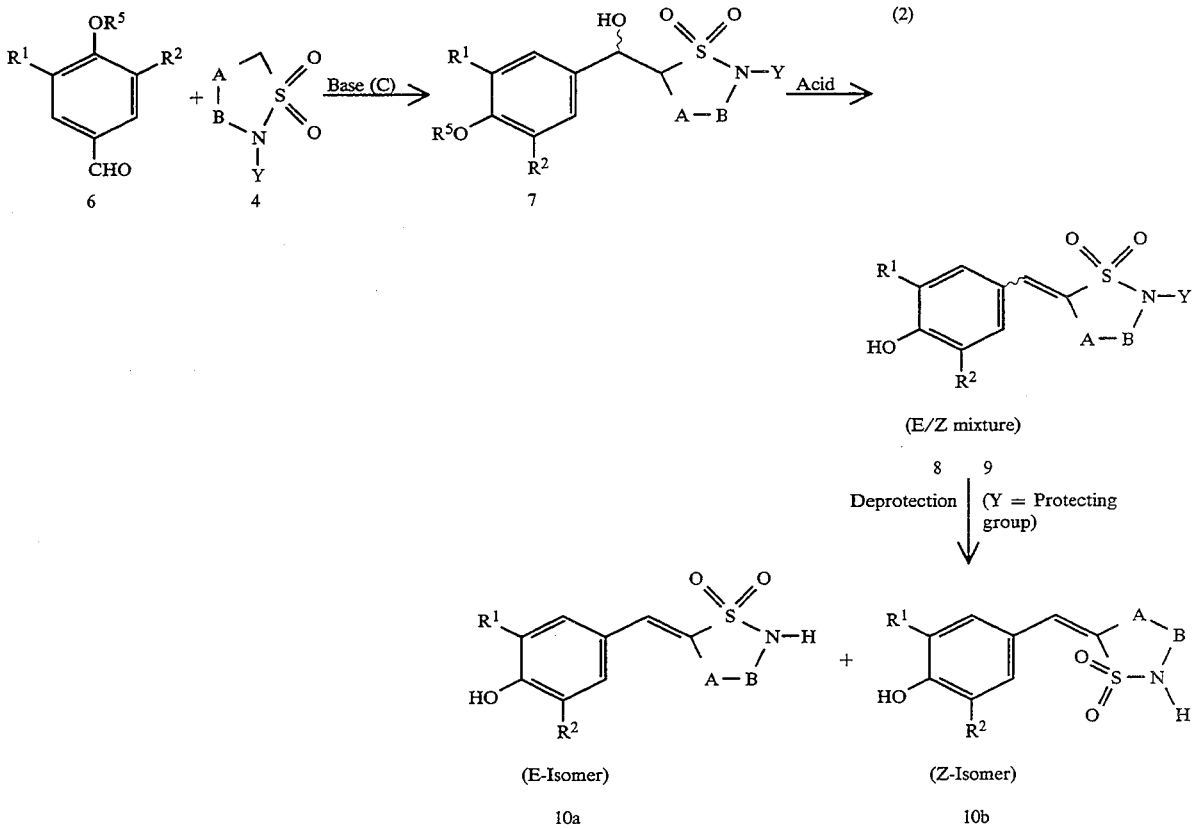

Base (C) in the above formula is as defined above. Y means an N-protecting group such as tert-butoxycarbonyl, benzyloxycarbonyl, benzyl,4-methoxybenzyl, 3,4-dimethoxybenzyl,4-nitrobenzyl and the like. The reaction conditions of the aldol reaction is similar to those described in the reaction scheme 1 above. Dehydrating and deprotecting reagents used in the conversion of aldol addition compound 7 to a mixture of compounds 10a and 10b include p-toluenesulfonic acid and trifluoroacetic acid, aluminium chloride, titanium tetrachloride and the like. The conditions such as reaction solvent, temperature and the like are similar to those described in reaction scheme 1. A mixture of (E)- and (Z)-isomers is deprotected to obtain compounds 10a In this reaction, a desired substituent $R^3$ is added to a compound of the present invention of formula I wherein D is >N- and $R^3$ is H to yield various derivatives. Base (D) used when $R^3$-X is an alkylating agent includes alkali metal bases such as sodium hydroxide, potassium hydroxide, sodium carbonate, potassium carbonate, sodium hydrogencarbonate, potassium hydrogen carbonate, lithium hydroxide and the like, or organic bases such as pyridine, triethylamine, diisopropylethylamine and the like. The alkylation is preferably carried out using sodium hydroxide or potassium carbonate in the presence of an appropriate quaternary ammonium salt as a phase transfer catalyst.

In case where R³X is an acylating agent, as base (D), an organic base such as pyridine, 4-dimethylaminopyridine, triethylamine, diisopropylethylamine or the like is used preferably.

When R³X is a carbamoylating agent or alkoxycarbonylating agent, as base (D), an organic lithium base such as n-butyllithium, lithium hexamethyldisilazane, lithium diisopropylamide is preferably utilized. The present invention is not limited to the use of these bases, but organic bases such as pyridine, triethylamine, diisopropylethylamine and the like or the alkali metal bases described above are also available.

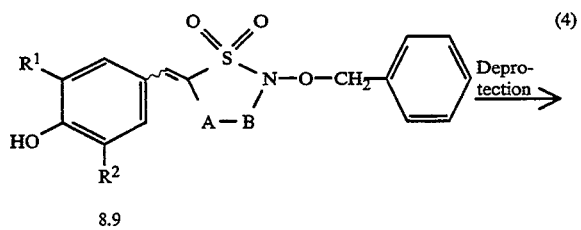

8.9

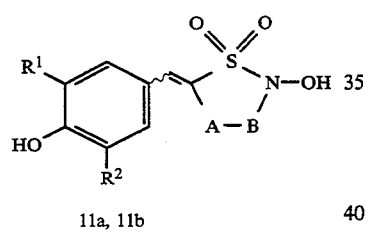

11a, 11b

Compounds 11a and 11b of the formula 1 wherein D is >N- and R³ is OH is obtained by de-benzylating compounds 8, and 9 which is carried out using a de-protecting agent. The deprotection is conducted by hydrogenation in the presence of palladium on carbon or platinum oxide, or by using a Lewis acid such as aluminium chloride, titanium tetrachloride or the like along with anisole, 2,6-di-tertbutylphenol and the like, if necessary.

Besides halogenated hydrocarbons such as dichloromethane, chloroform, dichloroethane and the like, nitromethane, benzene, toluene, xylene and the like can be also used as a reaction solvent.

The methods set forth in (1), (2), (3) and (4) above are generally applicable to the production of compounds I of the present invention and are specifically shown in Examples 1–35 below.

The compounds I of the present invention are also produced by treating a novel compound of the formula:

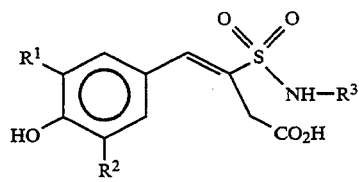

with ethyl chlorocarbonate or the like in the presence of a conventional dehydrating agent such as triethylamine to cleave the ring to yield a compound 8 of the formula:

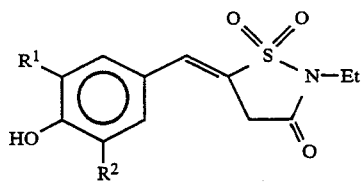

Examples of dehydrating agents include ethyl chloroformate, triethylamine, phosphorus oxychloride, thionyl chloride, DCC (dicyclohexylcarbodiimide) and the like. This method is also generally applicable to the production of the compounds of the formula I of the invention by selecting appropriate starting compound and reaction conditions.

The compound I of the present invention can be orally or parenterally administered as an anti-inflammatory agent. In case of oral administration, a compound of the present invention may be formulated into ordinary formulations in the form of solid such as tablets, powders, granules, capsules and the like; solutions; oily suspensions; liquid formulations such as syrups, elixirs and the like. In case of parenteral administration, a compound of the present invention may be formulated into an aqueous or oily suspension for injection or an external preparation. In preparing the formulations, conventional excipients, binders, lubricants, aqueous solvents, oily solvents, emulsifiers, suspending agents or the like may be used, and other additives, such as preservatives, stabilizers or the like may also be included.

Although appropriate daily dosage of the compound of the present invention varies depending upon the administration route, age, body weight and conditions of the patient, and the kind of disease to be treated, in case of adult patients, it can generally be between 10–500 mg, preferably 50–100 mg on oral administration, and 1–250 mg, preferably 5–10 mg on parenteral administration, in 1–5 divisions.

The following Examples are provided to further illustrate the present invention and are not to be construed as limiting thereof.

The abbreviations used in the examples have the following meanings: LDA=lithium diisopropylamide; MOM=methoxymethyl; p-TsOH=p-toluensulfonic acid; THF=tetrahydrofuran; DMF=N,N-Dimethylformamide; HMPA=hexamethylphosphoramide; LiHMDS=lithium hexamethyldisilazane; DBU=1,8-diazabicyclo[5,4,0]undec-7ene; and DIBAL=diisobutylalminium hydride.

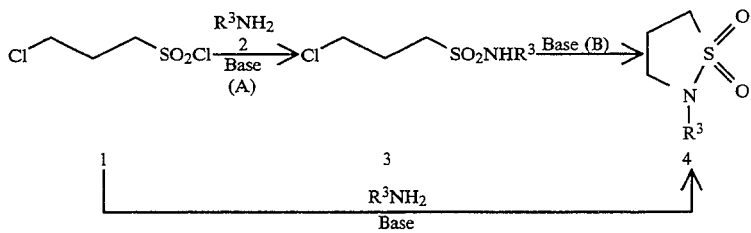

Preparation 1 (R³ =Et)

N-Ethyl-1,2-isothiazolidine-1,1-dioxide (4a)

To a solution of 3-chloropropylsulfonyl chloride 1(6.1 g,34.5mmol) in ether (25 ml) was added dropwise ethylamine (a 70% aqueous solution,4.4 g,68.3 mmol) with stirring under ice-cooling over 15 minutes. The resultant mixture was stirred for one hour at room temperature and concentrated in vacuo. Benzene (100 ml) was added to the residue and the solvent was distilled off in vacuo. To the residue was added ether (150 ml) and filtered to remove the insoluble material. The liltrate was distilled in vacuo to remove ether and 6.96 g (yield, about 100%) of crude N-ethyl-3-chloro propylsulfonamide (intermediate 3a) was obtained as colorless crystals (m.p.=30°–32° C.). To a solution of this intermediate 3a (6.96 g,34.5 mmol) in THF (50 ml) was slowly added sodium hydride (60% in oil,1.52 g,38.0 mmol) with stirring under ice-cooling over 15 minutes. The reaction mixture was stirred for another 30 minutes at room temperature. After the addition of ether (50 ml), the mixture was filtered to remove insoluble material and the filtrate was distilled in vacuo to remove solvent and to give 4.93 g (96%) of the objective compound 4a as a pale yellow oil.

IR(CHCl$_3$)cm$^{-1}$:3018,2976,2868,1452,1306,1220,1179,1129, 1015.

NMR( CDCl$_3$)δ: 1.24(3H,t, J=7.4Hz, CH$_3$), 2.28–2.42(2H,m, CH$_2$),3.10(2H,q,j=7.4z, CH$_2$), 3.15(2H,t,J=7.6Hz,CH$_2$), 3.22–3.29 (2H,m,CH$_2$).

Preparation 2 (R³=Me)

N-Methyl-1,2-isothiaZolidine-1,1-dioxide(4b )

3-Chloropropylsulfonyl chloride 1 (6.8 g,94.9 mmol), methylamine hydrochloride (13.5 g,200 mmol), and potassium carbonate (27.6 g,200 mmol) were added in turn to ethyl acetate (500 ml). After the addition of N-benzyltrimethylammonium chloride (about 200 mg), the resultant mixture was stirred for 2 hours at room temperature and dried over anhydrous sodium sulfate. The mixture was filtered through a small amount of silica gel and the filtrate was concentrated in vacuo to give 12 g (74%) of crude N-methyl-3-chloropropylsulfonamide (intermediate 3b) as a pale yellow oil.

To a solution of said intermediate 3b (11.79 g, 68.69 mmol) in benzene (300 ml) was added DBU (10.79 ml, 72.12 mM) and the resultant mixture was stirred for 24 hours at room temperature and filtered through a small amount of silica gel. The filtrate, when distilled in vacuo to remove solvent, gave 7.0 g (75%) of the objective compound 4b as a colorless solid (m.p.=36°–40° C.).

IR(CHCl$_3$)cm$^{-1}$:3016,1451,1307,1218,1187,1127.

NMR(CDCl$_3$)δ: 2.27–2.42(2H,m, CH$_2$),2.69 (3H,s, CH$_3$ ),3.11–3.20(2H,m,CH$_2$),3.22(2H,t,J=6.Hz,CH$_2$).

Preparation 3 (R³ =CH$_2$CH(CH$_3$)$_2$)

N-Isobutyl-1,2-isothiazolidine-1,1-dioxide (4c).

3-Chloropropylsulfonyl chloride 1 (7.08 g,40 mmol), isobutylamine (7.3 g,100 mmol) and sodium hydrogencarbonate (3.36 g,40 mmol) were added in turn to a mixture of ethyl acetate (200 ml) and water (20 ml). To the mixture was added N-benzyltrimethylammonium chloride (about 100 mg). The resultant mixture was stirred for 3 hours at room temperature and then treated in a manner similar to that described in Preparation 2 to give 8.19 g (96%) of crude N-isobutyl-3-chloropropylsulfonamide (intermediate 3c) as colorless crystals (m.p.=68°–69° C.).

To a solution of said intermediate 3c (4.27 g,20 mmol) in benzene (60 ml) was added DBU (3.3 ml,22 mmol) and the reaction mixture was treated in a manner similar to that described in Preparation 2 to give 3.37 g (95%) of the objective compound 4c as a colorless oil.

IR(CHCl$_3$)cm$^{-1}$:3016,2956,1465,1304,1226,1131,1024.

NMR(CDCl$_3$)δ: 0.95(6H, d, J=6.6Hz, (CH$_3$)$_2$),1.75–1.96(1H, m,CH), 2.27–2.42 (2H, m, CH$_2$),2.80(2H, d, J=7.4Hz, CH$_2$),3.10–3.19 (2H,m,CH$_2$),3.24 (2H, t, J=6.8Hz, CH$_2$).

Preparation 4 (R³=cyclopropyl)

N-Cyclopropyl-1,2-isothiazolidine-1,1-dioxide (4d)

3-Chloropropylsulfonyl chloride 1 (7.08 g,40 mmol), cyclopropylamine (6.0 g,105 mmol) and sodium hydrogencarbonate (3.7 g,44 mmol) were added to a mixture of ether (200 ml) and water (10 ml). The resultant mixture was treated in a manner similar to that described in Preparation 3 to give 8.0 g (about 100%) of crude N-cyclopropyl-3-chloropropylsulfonamide (intermediate 3d) as crystals (m.p.=48°–49.5° C.).

Said intermediate 3d (1.98 g,10 mmol) was reacted with DBU (1.65 ml,11 mmol) in benzene (30 ml) and the reaction mixture, when reacted in a manner similar to that described in Preparation 2, gave 1.40 g (87%) of the objective compound 4d as a pale yellow oil.

IR(CHCl$_3$)cm$^{-1}$:3016,1309,1221,1140, 1026.

NMR(CDCl$_3$)cm$^{-1}$: 0.60–0.85 (4H, m, cyclopropyl ),2.20–2.40 (3H, m, CH$_2$+CH),3.15–3.25 (2H, m, CH$_2$),3.32 (2H, t, J=6.6Hz, CH$_2$).

Preparation 5 (R³ =-CH$_2$CH$_2$CH$_3$ )

N-n-Propyl-1,2-isothiazolidine-1,1-dioxide (4e)

3-Chloropropylsulfonyl chloride 1 (7.08 g,40 mmol), n-propylamine (5.90 g,100 mmol), potassium carbonate (5.52 g,40 mmol) and a small amount of N-benzyltrimethylammonium chloride (about 100 mg) were stirred in a mixture of ether (200 ml) and water (20 ml) for 3 hours. The reaction mixture was treated in a manner similar to that described in Preparation 2 to give 8.0 g (about 100%) of crude N-n-propyl-3-chloropropylsulfonamide (intermediate 3e) as crystals (m.p.=47.5°–48° C).

Said intermediate 3e (2.0 g,10 mmol) was reacted with DUB (1.65 ml,11 mmol) in benzene (30 ml) in a manner similar to that described in Preparation 2 to give 1.41 g (86%) of the objective compound 4e as a pale yellow to colorless oil.

IR(CHCl$_3$)cm$^{-1}$:3018,2962,2868,1304,1224,1130,1019.

NMR(CDCl$_3$)δ:0.96(3H,t,J=7Hz,CH$_3$),1.52–1.72(2-H,m,CH$_2$),2.28–2.42 (2H,m,CH$_2$)2.94–3.04(2H,mCH$_2$), 3.10—3.20(2H, m, CH$_2$),3.25(2H,t, J=6.7Hz, CH$_2$ ).

Preparation 6 (R$^3$=CH$_3$)

N-Methoxy-1,2-isothiazolidine-1,1-dioxide (4f)

3-Chloropropylsulfonyl chloride 1 (7.08 g,40 mmol), O-methylhydroxylamine hydrochloride (3.76 g,40 mmol), and potassium carbonate (5.80 g,42 mmol) were reacted in a manner similar to that described in Preparation 5 to give 7.02 g (94%) of crude N-methoxy-3-chloropropylsulfonamide (intermediate 3f) as a colorless to pale yellow oil.

The intermediate 3f(6.25 g,33.3 mmol) was reacted with sodium hydride (60% in oil,1.47 g,36.7 mmol) in a manner similar to that described in Preparation 1 to give 3.70 g (73%) of the objective compound 4f as a colorless oil.

IR(CHCl$_3$)cm$^{-1}$:3022,1355,1249,1222,1165,1138,1035,1011.

NMR(CDCl$_3$)δ:2.37–2.50(2H,m,CH$_2$),3.-20–3.14(2H,mCH$_2$),3.50 (2H,t,J=7.0Hz,CH$_2$),3.81(3H,s,OCH$_3$).

Preparation 7 (R$^3$=OCH$_2$C$_6$H$_5$)

N-Benzyloxy-1,2-isothiazolidine-1,1-dioxide (4g)

3-Chloropropylsulfonyl chloride 1 (30.28 g,0.17 mol), O-benzylhydroxylamine hydrochloride (27.3 g,0.17 mol), potassium carbonate (50 g,0.36 mol) and tetrabutylammonium sulfate (about 500 mg) are reacted with each other in a mixture of ether and water (1:1) (100 ml) for 24 hours at room temperature and the reaction mixture was extracted with ethyl acetate. The extract was subjected to column chromatography on silica gel. From the fraction eluted with a mixture of ethyl acetate/n-hexane (1:4),18.4 g (41%) of crude N-benzyloxy-3-chloropropylsulfonamide (intermediate 3g) was obtained as a pale yellow oil.

To a solution of the above intermediate 3g (18.4 g,69.9 mmol) in THF (150 ml) was added sodium hydride (60% in oil,2.94 g,73.4 mmol) and the reaction was carried out in a manner similar to that described in Preparation 1. The product was subjected to column chromatography on silica gel. From the fraction eluted with a mixture of ethyl acetate/n-hexane (1:5),10.75 g (68%) of the objective compound 4g was obtained as a colorless crystal. M.p.=52°–54° C.

IR(CHCl$_3$)cm$^{-1}$:3022,2956,1453,1354, 1165,1140,1081,1000.

NMR(CDCl$_3$)δ: 2.30–2.48 (2H, m, CH$_2$),3.04–3.14 (2H,m, CH$_2$), 3.45 (2H,t, J=6.9Hz, CH$_2$),5.00(2H,s, OCH$_2$),7.30–7.45(5H, m, C$_6$H$_5$).

Preparation 8 (R$^3$=4-methoxybenzyl)

N-(4-Methoxybenzyl)-1,2-isothiazolidine-1,1-dioxide (4h)

3-Chloropropylsulfonyl chloride 1 (17.7 g,0.1 mol), p-methoxybenzylamine (15.0 g,0.11 mol), and sodium hydrogencarbonate (8.4 g,0.1 mol) were reacted in a mixture of ethyl acetate (400 ml) and water (40 ml) in a manner similar to that described in Preparation 3 to give 19.1 g (69%) of crude N-(4-methoxybenzyl)-3-chloropropylsulfonamide (intermediate 3h) as colorless crystals (m.p.=78°–80° C.).

The above intermediate 3g (11.11 g,40 mmol) was reacted with DBU (6.6 ml,40 mmol) in benzene (150 ml). The resultant mixture was treated in a manner similar to that described in Preparation 2 to give 8.89 g (92%) of the objective compound 4h as crystals (m.p.=48°–51° C.).

IR(CHCl$_3$)cm$^{-1}$:3016, 1612,1511,1304,1245,1136,1034.

NMR(CDCl$_3$)cm$^{-1}$:2.20–2.38(2H,m, CH$_2$),3.09 (2H,t,J=6.8Hz, CH$_2$), 3.14–3.24(2H,m,CH$_2$),3.81(3H, s,OCH$_3$),4.12(2H,s,CH$_2$),6.84–6.94(2H,m,CH$_2$), 7.22–7.32(4H,m4×aromatic-H).

Preparation 9 (R$^3$=3,4-dimethoxybenzyl)

N-(3,4-Dimethoxybenzyl)-1,2-isothiazolidine-1,1-dioxide (4i)

3-Chloropropylsulfonyl chloride 1 (8.85 g,50 mmol),3,4-dimethoxybenzylamine (9.0 ml,60 mmol) and potassium carbonate (4.13 g,30 mmol) were treated in a manner similar to that described in Preparation 2 to give 14.5 g (94%) of crude N-(3,4-dimethoxybenzyl)-3-chloropropylsulfonamide (intermediate 3i). The intermediate 3i, when treated in a manner similar to that described in Preparation 1, gave the objective compound 4i (yield: 69% ).

IR( CHCl$_3$)cm$^{-1}$: 3018, 1516,1307,1262,1225,1155,1138,1027.

NMR(CDCl$_3$)δ:2.22–2.38(2H,m,CH$_2$),3.11 (2H,t, J=6.7Hz, CH$_2$), 3.16–3.25(2H, m, CH$_2$),3.88 (3H, s, OCH$_3$),3.89(3H, s, OCH$_3$),4.12 (2H, s,CH$_2$),6.79–6.91(3H,m,3×aromatic-H).

Preparation 10 (R$^3$=C$_6$H$_5$)

N-Phenyl-1,2-isothiazolidine-1,1-dioxide (4j)

3-Chloropropylsulfonyl chloride 1 (1.456 g,8.23 mmol) was added dropwise to a solution of aniline (0.5 ml, 8.23 mmol) in pyridine (5 ml) with cooling at −20° to −30° C. over about 5 minutes. After the completion of the addition, the reaction mixture was stirred for another 45 minutes at room temperature. The reaction mixture was concentrated in vacuo and the residue was subjected to column chromatography on silica gel. From the fraction eluted with a mixture of ethyl acetate/n-hexane (1:2), 1.683 g (88%) of N-phenyl-3-chloropropylsulfonamide (intermediate 3j) was obtained as a yellow oil, which, when treated in a manner similar to that described in Preparation 1, gave the objective compound 4j as a pale yellow solid (yield 57%).

IR(CHCl$_3$)cm$^{-1}$:3020, 1598,1495,1315,1139.

NMR(CDCl$_3$)δ: 2.46–2.60(2H,m, CH$_2$),3.34–3.42(2H,m,CH$_2$ ), 3.78 (2H,t, J=6.6Hz, CH$_2$),7.10–7.40(5H, m, C$_6$H$_5$).

Preparation 11 ( $R^3$=4-chlorophenyl )

N-(4-Chlorophenyl)-1,2-isothiazolidine-1,1-dioxide (4k)

According to a similar method as that of Preparation 10, 3-chloropropylsulfonyl chloride was reacted with 4-chloroaniline in pyridine to give N-(4-chlorophenyl)-3-chloropropylsulfonamide (intermediate 3k) (yield 93%). The intermediate 3k, when treated with DBU in a similar manner as that described in Preparation 2, gave the objective compound 4k (yield 68%) as colorless crystals (m.p.=110.5°-111.5° C.).

IR(KBr)cm$^{-1}$:3010,2960,1595,1493,1300,1267,1131.
NMR(CDCl$_3$)δ:2.47-2.61(2H,m, CH$_2$),3.35-3.43(2H,m, CH$_2$),3.76 (2H,t,J=6.4Hz,CH$_2$),7.16-7.36(4H,m,4×aromatic-H).

Preparation 12 ($R^3$=2-pyridyl)

N-(2-Pyridyl)-1,2-isothiazolidine-1,1-dioXide (4l)

According to a similar method as that of Preparation 10, 3-chloropropylsulfonyl chloride was reacted with 2-aminopyridine to give N-(2-pyridyl)-3-chloropropyl-sulfonamide (intermediate 3l) as a pale yellow solid (yield 54%). To a solution of this intermediate 3l (2.138 g,9.11 mmol) in DMF (30 ml) was added sodium hydride (60% in oil,401 mg,10 mmol) under ice-cooling. The resultant mixture was stirred for 30 minutes at 85° C. and distilled in vacuo to remove the solvent. The residue was subjected to column chromatography on silica gel. From the fraction eluted with a mixture of ethyl acetate/n-hexane (1:1),1.806 (100%) of the objective compound 4l was obtained as a yellow solid.

IR(CHCl$_3$)cm$^{-1}$:3022, 1592,1473,1434,1139.
NMR(CDCl$_3$)δ: 2.47-2.60(2H, m, CH$_2$),3.43(2H, t, J=7.5Hz, CH$_2$). 4.05(2H,t, J=6.6Hz,CH$_2$),6.88-7.02(1H,m,CH),7.26-7.35(1H,m, CH),7.58-7.70(1H,m,CH),8.33(1H,d,J=4.4Hz,CH).

Preparation 13 ($R^3$=3-pyridyl)

N-(3-Pyridyl)-1,2-isOthizolidine-1,1-dioxide (4m)

According to a similar method as that of Preparation 10, 3-chloropropylsulfonyl chloride (17.28 g, 41.1 mmol) was reacted with 3-aminopyridine (4.6 g,49.3 mmol) in pyridine (15 ml) to give 4.50 g (46%) of crude N-(3-pyridyl)-3-chloropropylsulfonamide (intermediate 3m) as a colorless solid.

The intermediate 3m (232 mg,0.988 mmol) was treated with sodium hydride (60% in oil,43.5 mg,1.09 mmol) in DMF (5 ml) in a similar manner as that described in Preparation 12 to give 190 mg (97%) of the objective compound 4m as a colorless solid.

IR(CHCl$_3$)cm$^{-1}$:3022,2960,1590,1484,1428,1319,114-2.
NMR(CDCl$_3$)δ:2.53-2.67(2H,m, CH$_2$),3.38-3.45(2H, m, CH$_2$), 3.83(2H,t,J=6.6Hz,CH$_2$),7.28-7.36(1H,m,CH ),7.73-7.79 (1H,m, CH),8.41 (1H,d,J=4.6Hz,CH),8.46(1H,d, J=2.4Hz,CH).

Preparation 14 ($R^3$=4-pyridyl)

N-(4-Pyridyl)-1,2-isothiazolidine-1,1-dioxide (4n)

To a solution of 3-chloropropylsulfonyl chloride 1(3 ml,24.7 mmol) and 4-aminopyridine (2.32 g,24.7 mmol) in DMF (25 ml) was slowly added sodium hydride (60% in oil, 2.17 g,54.3 mmol) over about 5 minutes with stirring under ice-cooling. After the stirring was continued for another minutes at 50° C., the reaction mixture was subjected to column chromatography on silica gel. From the fraction eluted with a mixture of methylene chloride/methanol (10:1),1.294 (27%) of the objective compound 4n was obtained as a yellow solid.

IR(CHCl$_3$)cm$^{-1}$: 3024,2956,1597,1504,1320,114-3.
NMR(CDCl$_3$)δ:2.53-2.67(2H,m, CH$_2$),3.43(2H,t,j=7.6Hz,CH$_2$), 3.81(2H,t,J=6.6Hz,CH$_2$),7.08(2H,d,J=5.4Hz,CH),8.4-9(2H,d, J=5.4Hz,CH).

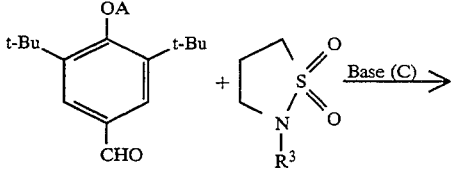

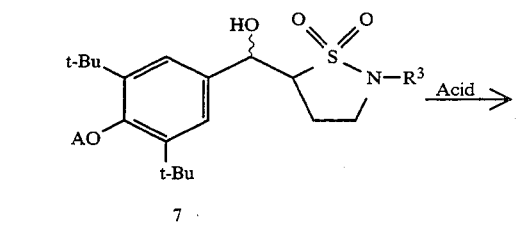

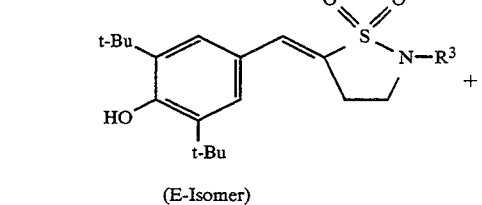

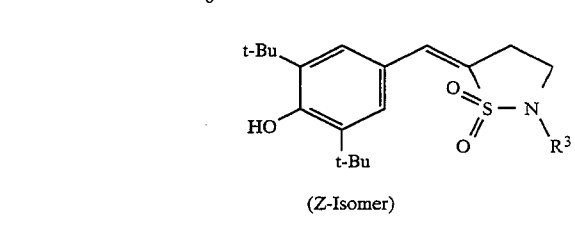

Example 1 ($R^3$=Et)

(E)-2-Ethyl-5-(3,5-di-tert-butyl-4-hydroxy)benzylidene-1,2-isothiazolidine-1,1-dioxide (8a) and its (Z)-isomer (9a)

To diisopropylamine (15.5 ml,110.6 mmol) was added dropwise in an ice-water bath n-butyllithium in hexane (1.6 M,69.5 ml,111 mmol) over 20 minutes with stirring. After completion of the addition, stirring was conducted for another 15 minutes and the reaction mixture was cooled to −78° C. followed by addition of THF (100 ml). To the reaction mixture was added dropwise a solution of N-ethyl-1,2-isothiazolidine-1,1-dioxide 4a (15 g,100.5 mmol),3,5-di-tert-butyl-4-methoxymethoxybenzaldehyde 6 (25 g,90.5 mmol) and HMPA (30 ml) in the THF (70 ml) over 15 minutes with stirring. The reaction mixture was stirred for another 30 minutes at the same temperature, warmed to room temperature, poured into cold 2N-HCl (100 ml) and extracted with ethyl acetate (2×250 ml). The ethyl acetate phase was washed with a dilute aqueous solution of sodium hydrogencarbonate (300 ml) and a saturated brine (300 ml), dried over anhydrous sodium sulfate and distilled in vacuo to remove the solvent. The residue, when purified by column chromatography on silica gel eluting with n-hexane/ethyl acetate (4:1 to 1:1), gave 21.3 g (55%) of aldol addition compound 7a as a colorless solid.

To a solution of the addition compound 7a (8.5 g, 19.9 mmol) in toluene (150 ml) was added p-toluenesulfonic acid hydrate (2.49 g,13 mmol). The resultant mixture was heated to reflux for 30 minutes and then poured into a dilute aqueous solution of sodium hydrogencarbonate (150 ml) and extracted with ethyl acetate (150ml×2). The organic layer was washed with water (150 ml) and a saturated brine (150 ml), dried over anhydrous sodium sulfate and distilled in vacuo to remove the solvent. The residue was subjected to column chromatography on silica gel. From the fraction eluted with n-hexane/ethyl acetate (3:1), the objective compounds 9a (376 mg,7%) and 8a (2.59 g,36%) were obtained in turn.

Compound 8a: m.p.=135°–137° C.
IR(KBr)cm$^{-1}$:3610,3440,2970,2880,1645,1597,1430,1290,1173,1151,1139.
NMR(CDCl$_3$)δ:1.-29(3H,t,J=7.2Hz,CH$_3$),1.45(18H,s,2=Bu$^t$),3.-07-3.19(4H,m,CH$_2$),m3.28(2H,q.J=7.2HzCH$_2$),5.50(1-H,,s,OH),7.24-726(3H,m,2×aromatic-H,CH).
Elementary analysis(C$_{20}$H$_{31}$NO$_3$S)
Calcd:C,65.71;H,8.55;N,3.83;S,8.77
Found:C,65.65;H,8.43;N,3.85;S,8.78.

Compound 9a: m.p.=137°–138° C.
IR(KBr)cm$^{-1}$:3560,2975,1637,1600,1431,1289,1275,1168, 1150,1111.
NMR(CDCl$_3$)δ:1.26(3H,t,J=7.2Hz,CH$_3$),1.45(18H,-s,2×Bu$^t$),3.00 (2H,dt, J=2.0,6.0Hz,,CH$_2$),3.15(2H,q,J=7.2Hz,CH$_2$),3.25(2H,-t, J=6.0Hz,CH2),5.47(1H,s,OH),6.73(1H,t,J=2.0Hz,CH-),7.52(2H,s, 2×aromatic-H).
Elementary analysis(C$_{20}$H$_{31}$NO$_3$S)
Calcd:C,65.71;H,8.55;N,3.83;S,8.77
Found:C,65.68;H,8.43;N,3.61;S,8.66.

Example 2 (R$^3$=CH$_3$)

(E)-2-Methyl-5-(3,5-di-tert-butyl-4-hydroxy)benzylidene-1,2-isothiazolidine-1,1-dioxide (8b) and its (Z)-isomer (9i)

According to a similar method as that of Example 1, an aldol reaction was carried out using compound 6 (3.34 g,12 mmol) and N-methyl-1,2-isothiazolidine-1,1-dioxide 4b (1.35 g,10 mmol) to give 1.65 g (40%) of addition compound 7b. To a solution of the addition compound 7b (1.60 g, 3.87 mmol) in toluene (30 ml) was added p-toluenesulfonic acid hydrate (160 mg) and the resultant mixture was heated to reflux for 30 minutes. The reaction product was subjected to column chromatography on silica gel. From the fraction eluted with a mixture of n-hexane/ethyl acetate (3:7 ), the objective compounds 8b (580 mg,43% ) and 9b (200 mg,15% ) were obtained.

Compound 8b: m.p.=168°–170° C.
IR(CHCl$_3$)cm$^{-1}$:3620, 2956,1435,1292,1218,1149.
NMR(CDCl$_3$)δ:1.45(18H,s,2×Bu$^t$),2.76(3H,s,NCH$_3$-), 3.07-3.18(2H,m, CH$_2$),3.20-3.32(2H,m,CH$_2$),5.51(1H,s,OH ),7.23-7.29(3H,m, 2×aromatic-H,CH ).
Elementary analysis (C$_{19}$H$_{29}$NO$_3$S )
Calcd:C,64.92;H,8.32;N,3.98; S,9.12
Found:C,64.62;H,8.31;N,3.95;S,9.14.

Compound 9b: m.p.=152°–163° C.
IR(CHCl$_3$)cm$^{-1}$:3622,2956,1433,1293,1241,1160,1010.
NMR(CDCl$_3$)δ:1.45(18H,s,2×Bu$^t$),2.75 (3H,s,NCH$_3$),2.95-3.05 (2H, m,CH$_2$),3.16-3.26(2H,m, CH$_2$),5.49(1H,s,OH). 6.75 (1H,t, J=2.2Hz, CH),7.58(2H,s,2×aromatic-H).
Elementary analysis (C$_{19}$H$_{29}$NO$_3$S)
Calcd:C,64.92;H,8.32;N,3.98;S,9.12
Found:C,64.61;H,8.29;N,3.95;S,9.07.

Example 3 (R$^3$=CH$_2$CH (CH$_3$)$_2$)

(E) -2-Isobutyl-5-(3,5-di-tert-butyl-4-hydroxy) benzylidene-1,2-isothiazolidine-1,1-dioxide (8c)

According to a similar method as that of Example 1, an aldol reaction was carried out using compound 6 (2.78 g,19 mmol) and N-isobutyl-1,2-isothiazolidine-1,1-dioxide 4c (1.95 g,11 mmol) to give 3.67 g (81%) of addition compound 7c.

This addition compound 7c (3.60 g,7.9 mmol) in toluene (50 ml) was treated with p-toluenesulfonic acid hydrate (360 mg) in a similar manner as that of Example 1. The product was subjected to column chromatography on silica gel and from the fraction eluted with a mixture of n-hexane-ethyl acetate (1:3), the objective compounds 8c (1.30 g,42%) was obtained.

M.p.=167°–170° C.
IR(CHCl$_3$)cm$^{-1}$:3620,2956,1646,1435,1289,1240,1148,1081.
NMR(CDCl$_3$)δ:0.97(6H,d,J=6.4Hz, (CH$_3$)2),1.45(18H,s,2×Bu$^t$), 1.81-2.02(1H,m,CH),2.87(2H,d, J=7.4Hz, CH$_2$),3.06-3.18 (2H,m CH$_2$),3.22-3.33(2H,m,CH$_2$),5.50(1H,s,OH),7.-23-7.27(3H,m, 2×aromatic-H,CH).
Elementary analysis(C$_{22}$H$_{35}$NO$_3$S)
Calcd:C,67.14;H,8.96;N,3.56;S,8.15
Found:C,66.85;H,8.99;N,3.58;S,8.11.

Example 4 (R$^3$=cyclopropyl)

(E)-2-Cyclopropyl-5-(3,5-di-tert-butyl-4-hydroxy) benzylidene-1,2-isothiazolidine-1,1-dioxide (8d)

According to a similar method as that of Example 1, an aldol reaction was carried out using compound 6 (2.67 g,9.6 mmol) and N-cyclopropyl-1,2-isothiazolidine-1,1-dioxide 4d (1.29 g,8.0 mmol) to give 3.09 g (88%) of addition compound 7d. The addition compound 7d (3.0 g,7 mmol) in toluene (50 ml) was treated together with ptoluenesulfonic acid hydrate (300 mg). The reaction product was purified in a similar manner as that of Example 3 to give 1.03 g (40%) of the objective compound 8d.

M.p.=202°–204° C.
IR(CHCl$_3$)cm$^{-1}$:3620,2956,1434, 1297,1237,1145.
NMR(CDCl$_3$)δ:0.68-0.90(4H,m,2×CH$_2$), 1.44(18H,s,2×Bu$^t$),
2.28-2.40(1H,m,CH),3.08(2H,dt,J=2.6,6.7Hz,CH$_2$),3.3-6(2H,t, J=6.7Hz,CH$_2$),5.51(1H,s,OH),7.20-7.25(3H,m,-2×aromatic-H,CH).
Elementary analysis(C$_{21}$H$_{31}$ NO$_3$S)
Calcd:C,66.81;H,8.28;N,3.71;S,8.49
Found:C,66.67;H,8.29;N,3.71;S,8.38.

Example 5 ($R^3 = CH_2{}_2CH_3$)

(E)-2-n-Propyl-5-(3,5-di-tert-butyl-4-hydroxy). benzylidene-1,2-isothiazolidine-1,1-dioxide (8e) and its (Z)-isomer (9e)

According to a similar method as that of Example 1, an aldol reaction was carried out using compound 6 (2.78 g,10 mmol) and N-n-propyl-1,2-isothiazolidine-1,1-dioxide 4e (1.35 g,8.27 mmol) to give 1.5 g (41%) of addition compound 7e. The addition compound 7e was treated with p-toluenesulfonic acid hydrate (400 mg) in a manner similar to that described in Example 1. The reaction product was subjected to column chromatography on silica gel and from the fraction eluted with a mixture of n-hexane-ethyl acetate (1:4 ), the objective compounds 8e (810 mg,26% ) and 9e (120 mg,3.8% ) were obtained.

Compound 8e: m.p.=181°–183° C.
IR($CHCl_3$)cm$^{-1}$:3616,2954, 1435,1289,1146.
NMR ($CDCl_3$)cm$^{-1}$:0.98(3H,t,J=7.4Hz,$CH_3$), 1.45(18H,s,2×$BU^t$) 1.57–1.78 (2H,m,$CH_2$),2.98–3.20(4H,m,2×$CH_2$),3.22–3.34(2H,m,$CH_2$),5.50(1H,s,OH),7.23–7.27(3H,m,2×aromatic-H,CH ).
Elementary analysis ($C_{21}H_{33}NO_3S$)
Calcd:C,66.45;H,8.76;N,3.69;S,8.45
Found: C,66.25;H,8.74;N,3.70;S,8.33.
Compound 9e: m.p.=123°–124.5° C.
IR( $CHCl_3$)cm$^{-1}$:3622,2958,1433,1289,1164.
NMR($CDCl_3$)δ:0.96(3H,t,J=7.4Hz,$CH_3$),1.45(18H,s,2×$Bu^t$),1.55–1.72(2H,m,$CH_2$),2.95–3.08(4H,m,2$CH_2$),3.20–3.29(2H,m,$CH_2$),5.47(1H,s,OH),6.74(1H,t,J=2.1Hz,CH),7.57(2H,s, 2×aromatic-H).

Example 6 ($R^3 = OCH_3$)

(E)-2-Methoxy-5-(3,5-di-tert-butyl-4-hydroxy)benzylidene-1,2-isothiazolidine-1,1-dioxide (8f) and its (Z)-isomer(9f)

According to a similar method as that of Example 1, an aldol reaction was carried out using compound 6 (5.56 g,20 mmol) and N-methoxy-1,2-isothiazolidine-1,1-dioxide 4f (3.32 g,22 mmol) to give 6.89 g (80%) of addition compound 7f. The addition compound 7f (6.89 g,16 mmol) in toluene (100 ml) was treated with p-toluenesulfonic acid hydrate (1 g) in a manner similar to that described in Example 1. The reaction product was subjected to column chromatography on silica gel and from the fraction eluted with a mixture of n-hexane-ethyl acetate (6:1), the objective compounds 8f (2.40 g,41%) and 9f(500 mg,8.5%) were obtained.

Compound 8f:m.p.=166°–168° C.
IR($CHCl_3$)cm$^{-1}$:3616,2952,1639,1436,1340,1240,1158,1002
NMR($CDCl_3$)δ:1.45(18H,s,2×But),3.11(2H,dt,J=2.-2,6,8Hz,$CH_2$), 3.66(2H,t,J=7Hz,$CH_2$),3.81(3H,s,$OCH_3$),5.55(1H,s,OH),7.25–7.35(3H,m,3×aromatic-H,CH).
Elementary analysis($C_{19}HD_{29}NO_4S$)
Calcd:C,62.10;H,7.95;N,3.81;S,8.72
Found:C,61.90;H,7.88;N,3.91;S,8.67.
Compound 9f: m.p.=173°–176° C.
IR($CHCl_3$)cm$^{-1}$:3616,2950, 1431,1341,1240, 1155,1010.
NMR($CDCl_3$)δ:1.45(18H,s,2×$Bu^t$),3.12(2H,dt,J=2.-2,6,8Hz,$CH_2$), 3.61(2H,t,J=6.8Hz,$CH_2$),3.61(3H,s,$OCH_3$),5.49(1H,s,OH),7.01 (1H,t,J=2.2Hz,CH),7.49(2H,s,2×aromatic-H).

Elementary analysis($C_{19}H_{29}NO_4S$×0.4$H_2O$)
Calcd:C,60.90;H,8.02;N,3.74;S,8.56
Found:C,61.08;H,7.76;N,3.75;S,8.61.

Example 7 ($R_3 = OCH_2C_6H_5$)

(E)-2-Benzyloxy.-5-(3,5-di-tert-butyl-4-hydroxy) benzylidene-1,2-isothiazolidine-1,1-dioxide (8g)

According to a similar method as that of Example 1, an aldol reaction was carried out using compound 6 (15 g,54 mmol ) and N-benzyloxy-1,2-isothiazolidine-1,1-dioxide 4g (10.23 g,45 mmol ) to give 15.51 g (68% ) of addition compound 7g. The addition compound 7g (10.21 g,20.2 mmol ) in toluene (150 ml) was treated with p-toluenesulfonic acid hydrate (1 g) in a manner similar to that described in Example 1. The reaction product was filtered through a small amount of silica gel, and the filtrate was concentrated in vacuo to give 5.32 g (59%) of the objective compound 8 g ( m.p.=134°–135° C.).
IR($CHCl_3$)cm$^{-1}$:3620, 2956,1639,1436,1339,1241,1159.
NMR($CDCl_3$)δ:1.44(18H,s,2×$Bu^t$),3.09(2H,dt,J=2.-6,6.8Hz,$Ch_2$), 3.58(2H,t,J=6.8Hz,$CH_2$),5.02(2H,s,$OCH_2$),5.53(1H,s,OH),7.25–7.45(8H,m,7×aromatic-H, CH ).
Elementary analysis ($C_{25}H_{33}NO_4S$)
Calcd:C,67.69;H,7.50;N,3.16;S,7.23
Found:C,67.52;H,7.59;N,3.18;S,7.16.

Example 8 ($R^3$ =4-methoxybenzyl) cl (E)-2-(4-Methoxybenzyl)-5-(3,5-di-tert-butyl-4-hydroxy benzylidene-1,2-isothiazolidine-1,1-dioxide (8h) and its (Z)-isomer (9h)

According to a similar method as that of Example 1, an aldol reaction was carried out using compound 6 (9 g, 32 mmol) and N-(4-methoxybenzyl)-1,2-isothiazolidine-1,1-dioxide 4h (7.24 g,30 mmol) to give 13.61 g (84%) of addition compound 7h. The addition compound 7h (12.6 g, 24.2 mmol) in toluene (150 ml) was treated with p-toluenesulfonic acid hydrate (1.3 g) in a manner similar to that described in Example 1 to give 8.83 g of a mixture of the objective compounds 8h and 9h.

Example 9 ($R^3$=3,4-dimethoxybenzyl)

(E)-2-(3,4-DimethoxybenZyl)-5-(3,5-di-tert-butyl-4-hydroxy) benzylidene-1,2-isothiazolidine-1,1-dioxide (8i) and its (Z)-isomer (9)

According to a similar method as that of Example 1, an aldol reaction was carried out using compound 6 (5.6 g,20 mmol) and N-(3,4-dimethoxybenzyl)-1,2-isothiazolidine-1,1-dioxide 4i (5.85 g,21.6 mmol) to give 9.25 g (78%) of addition compound 7i. The addition compound 7i (4 g,7.3 mmol), when subjected to dehydration and deprotection in a manner similar to that described in Example 1, gave a mixture of the objective compounds 8i and 9i (2.5 g).

Example 10 ($R^3 = C_6H_5$)

(E)-2-Phenyl-5-(3,5-di,tert-butyl-4-hydroxy)benzylidene-1,2-isothiazolidine-1,1-dioxide (8j) and its (Z)-isomer (9j)

According to a similar method as that of Example 1, an aldol reaction was carried out using compound 6 (2.47 g,8.88 mmol) and N-phenyl-1,2-isothiazolidine-1,1-dioxide 4j (2.19 g,11.10 mmol) to give 3.184 g (75%) of addition compound 7j. The addition compound 7j (3.184 g,6.69 mmol) in toluene (100 ml) was treated with p-toluenesulfonic acid hydrate (750 mg) to give the objective compounds 8j (667 mg,24%) and 9j (110 mg,4%).

Compound 8j: m.p.=195°-196° C.
IR(KBr)cm$^{-1}$:3560,3520,2960,1636,1593,1492,1430,1295,1268,1105,1092.
NMR(CDCl$_3$)δ:1.47(18H,s,2×Bu$^t$),3.31(2H,dt,J=2.6,6.6Hz,CH2), 3.80(2H,t,J=6.6Hz,CH$_2$),5.54(1H,s,OH),7.17-7.26(2H,m, aromatic-H,CH),7.29(2H,s,2×aromatic-H),7.38-7.42(4H,m, 4×aromatic-H).
Elementary analysis(C$_{24}$H$_{31}$NO$_3$S×0.1H$_2$O)
Calcd:C,69.39;H,7.61;N,3.37;S,7.72
Found:C,69.27;H,7.60;N,3.39;S,7.61.
Compound 9j:m.p.=172 -174° C.
IR(KBr)cm$^{-1}$:3540,2960,1629,1598,1503,1435,1305,1255, 1140,1118.
NMR(CDCl$_3$)δ:1.44(18H,s,2×Bu$^t$),3.17(2H,dt,J=2.0, 6.2Hz, CH$_2$),3.77(2H,t,J=6.2Hz,CH$_2$),5.49(1H,s,OH),6.84(1H,t,J=2.0Hz, CH),7.18-7.40(5H,m,5×aromatic-H),7.59(2H,s,2×aromatic-H).
Elementary analysis (C$_{24}$H$_{31}$NO$_3$S×0.1H$_2$O)
Calcd:C,69.39;H,7.61;N,3.37;S,7.72
Found:C,69.28;H,7.56;N,3.39;S,7.69.

Example 11 (R$^3$=4-chlorophenyl)

(E)-2- (4-Chlorophenyl)-5-(3,5-di-tert-butyl-4-hydroxy) benzylidene-1,2-isothiazolidine-1,1-dioxide (8k ) and its (Z)-isomer (9k)

According to a similar method as that of Example 1, an aldol reaction was carried out using compound 6 (2.25 g,8.09 mmol ) and N-(4-chlorophenyl )-1,2-isothiazolidine-1,1dioxide 4k (2.34 g,10.1 mmol) to give 2.54 g (62%) of addition compound 7k. The addition compound 7k (2.53 g, 4.96 mmol ) in toluene (70 ml ) was treated with p-toluenesulfonic acid hydrate (250 mg) to give the objective compounds 8k (859 mg,39% ) and 9k (263 mg,12% ).

Compound 8k:m.p.=245°-246° C.
IR(KBr)cm$^{-1}$:3560, 2960, 1644, 1592,1491,1430, 1280, 1105, 1090.
NMR(CDCl$_3$)δ:1.46(18H,s,2×Bu$^t$),3.30(2H,dt, J=2.6,6.6Hz, CH$_2$), 3.76 (2H,t,J=6.6Hz,CH$_2$),5.55(1H,s,OH),7.28(2H,s,2×aromatic-),H 7.26-7.40(5H,m,4×aromatic-H,CH).
Elementary analysis (C$_{24}$H$_{30}$NO$_3$SCl)
Calcd:C,64.34;H,6.75;N,3.13;S,7.16;Cl7.91
Found:C,64.59;H,6.78;N,3.28;S,7.17;C1,7.87.
Compound 9k: m.p.=207°-209° C.
IR(KBr)cm$^{-1}$:3540,2955,1635,1595,1494,1432,1300,1270,1130.
NMR(CDCl$_3$)δ:1.44(18H,s,2×But),3.17(2H,dt,J=2.0,6.4Hz,CH$_2$), 3.73(2H,t,J=6.4Hz,CH$_2$),5.51(1H,s,OH),6.86(1H,t,J=2.0Hz,CH), 7.34(4H,s,4×aromatic-H),7.57(2H,s,2×aromatic-H).
Elementary analysis (C$_{24}$H$_{30}$NO$_3$SCl)
Calcd:C,64.34;H,6.75;N,3.13;S,7.16;Cl,7.91
Found:C,64.14;H,6.80;N,3.23;S,7.06,Cl,7.95.

Example 12 (R$^3$=2-pyridyl)

(E)-2-(2-Pyridyl)-5-(3,5-di-tert-butyl-4-hydroxy benzylidene-1,2-isothiazolidine-1,1-dioxide (81) and its (Z)-isomer (91)

According to a similar method as that of Example 1, an aldol reaction was carried out using compound 6 (208 mg,0.75 mmol) and N-(2-pyridyl)-1,2-isothiazolidine-1,1-dioxide 41 (149 mg,0.75 mmol) to give 233 mg (65%) of addition compound 71. The addition compound 71 (231 mg, 0.485 mmol) in toluene (5 ml) was treated with p-toluenesulfonic acid hydrate (60 mg) to give the objective compounds 81 (96 mg,48%) and 91 (19 mg,9%).

Compound 81:m.p.=177°-179° C.
IR(KBr)cm$^1$:3570,2960,1646,1600,1587,1472,1431,1300,1105,1085.
NMR(CDCl$_3$)δ:1.47(18H,s,2×Bu$^t$),3.31(2H,dt,J=2.4, 6.8Hz,Ch$_2$), 4.08(2H,t,J=6.8Hz,CH$_2$),5.55(1H,s,OH),6.9-7.05(1H,m,CH),728(2H,s,2×aromatic-H ),7.38(1H,t,J=2.4Hz, Py-H), 7.55-7.74(2H,m,2×Py-H),8.33-8.36(1H,m,Py-H).
Elementary analysis (C$_{23}$H$_{30}$N$_2$O$_3$S)
Calcd:C,66.63;H,7.29;N,6.76;S,7.73
Found:C,66.31;H,7.30;N,6.72;S,7.66.
Compound 91:m.p.=198°-199 ° C.
IR(KBr)cm$^{-1}$:3550, 2960, 1626,1594, 1570, 1470, 1429,1312, 1302,1272,1140, 1115.
NMR(CDCl$_3$)δ:1.46(18H,s,2×Bu$^t$),3.16(2H,dt,J=2.0,6.6Hz,CH$_2$), 4.06(2H,t,J=6.6Hz,CH$_2$),5.51(1H,s,OH),6.87(1H,t,J=2.0Hz, CH), 6.96-7.04(1H,m,Py-H),7.58(2H,s,2×aromatic-H ),7.54-7.73 (2H,m,2×Py-H ),8.32-8.37(1H,m,Py-H).
Elementary analysis(C$_{23}$H$_{30}$N$_2$O$_3$S)
Calcd:C,66.63;H,7.29; N,6.76;S,7.73
Found:C,66.40;H,7.23;N,6.71;S,7.53.

Example 13 (R$^3$=3-pyridyl)

(E)-2- (3-Pyridyl)-5-(3,5-di-tert-butyl-4-hydroxy) benzylidene-1,2-isothiazolidine-1,1-dioxide (8m )

According to a similar method as that of Example 1, an aldol reaction was carried out using compound 6 (1.474 g,5.30 mmol) and N-(3-pyridyl)-1,2-isothiazolidine-1,1-dioxide 4m (1.051 g,5.30 mmol) to give 1.522 g (60%) of addition compound 7m. The addition compound 7m (1.522 g,3.19 mmol) in toluene (40 ml) was treated with p-toluenesulfonic acid hydrate (400 mg) to give 358 mg (27%) of the objective compound 8m.
M.p.=207°-209° C.
IR(KBr)cm$^{-10}$:3625,3040,2960,1640,1590,1480,1431,1305,1152.
NMR(CDCl$_3$)δ:1.47(18H,s,2×Bu$^t$),3.36(2H,dt,J=2.4,6,4Hz, CH$_2$),3.84(2H,t,J=6.4Hz,CH$_2$),5.59(1H,s,OH),7.29(2H,s, 2×aromatic-H),7.29-7.40(2H,m,CH,Py-H),7.84-7.93(1H,m,Py-H), 8.37-8.64(2H,m,2×Py-H).
Elementary analysis(C$_{23}$H$_{30}$N$_2$O$_3$S)
Calcd:C,66.63;H,7.29;N,6.76;S,7.73
Found:C,66.31;H,7.27;N,6.69;S,7.47.

Example 14 (R$^3$ =4-pyridyl)

(E)-2-(4-Pyridyl)-5-(3,5-di-tert-butyl-4-hydroxy) benzylidene-1,2-isothiazolidine-1,1-dioxide (8n)

According to a similar method as that of Example 1, an aldol reaction was carried out using compound 6 (2.59 g,9.36 mmol) and N-(4-pyridyl)-1,2-isothiazolidine-1,1-dioxide 4n (2.05 g,10.4 mmol) to give 2.721 g (61%) of addition compound 7n. The addition compound 7n (1.65 g, 3.46 mmol) in toluene (80 ml) was treated with p-toluenesulfonic acid hydrate (433 mg) to give 658 mg (46%) of the objective compound 8n.

M.p.=213°-214.5° C.
IR(kBr)cm⁻¹:3400,2955,1643,1591,1502,1437,1316,1153.
NMR(CDCl₃)δ:1.47(18H,s,2×Buᵗ),3.37 (2H, dt,J=2.2, 6.8Hz, CH₂ ), 3.82(2H,t,J=6.8Hz,CH₂ ),5.61(1H,s,OH),7.21-7.25 (4H,m,2×aromatic-H,2×Py-H ),7.42 (1H,t,J=2.2Hz,CH),8.50-8.58(2H,m,2×Py-H).
Elementary analysis (C₂₃H₃₀N₂O₃S)
Calcd:C,66.63;H,7.29;N,6.76;S,7.73
Found:C,66.46;H,7.18;N;6.66;S,7.49.

broad,NH),5.52(1H, s,OH), 7.22-7.27(3H,m,2×aromatic-H,CH).
Elementary analysis (C₁₈H₂₇NO₃S×0.35H₂O)
Calcd:C,62.89;H,8.12;N,4.07;S,9.38
Found:C,63.10;H,7.90;N,4.17;S,9.11.

Example 16 (R³H) (Y=4-methoxybenzyl)

(Z)-5-(3,5-Di-tert-butyl-4-hydroxy)benzylidene-1,2-isothiazolidine-1,1-dioxide (10b)

To a solution of the addition compound 7h (13.16 g,25.3 mmol) of the aldol reaction obtained in a manner

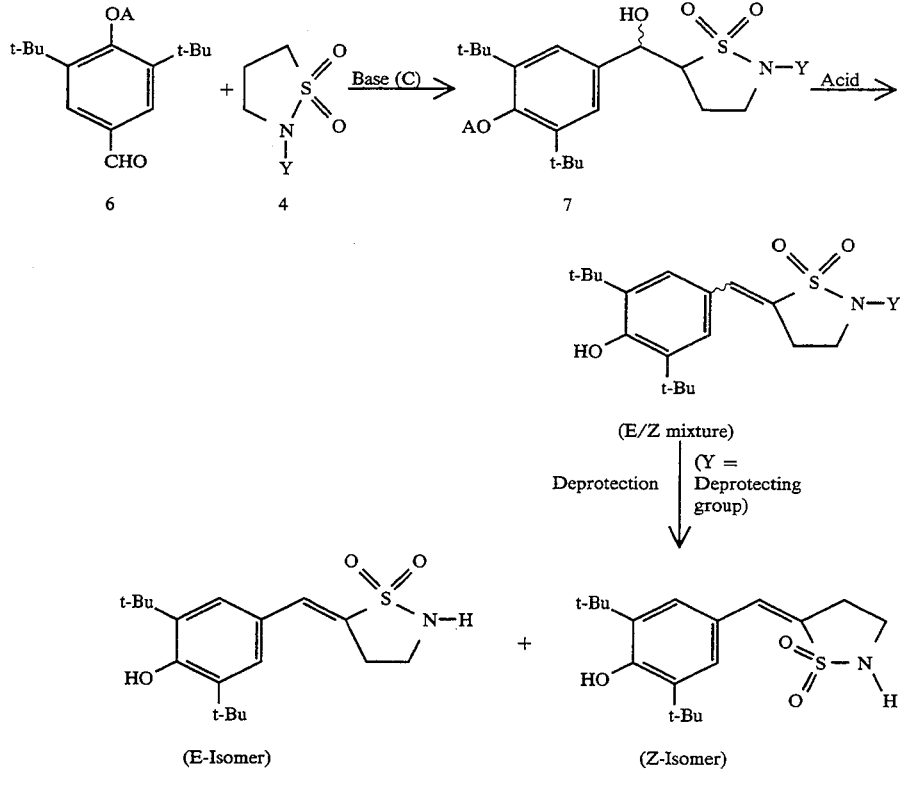

Example 15 (R3=H) (Y=CO₂C(CH₃)₃)

(E)-5-(3,5-Di-tert-butyl-4-hydroxy)benzylidene-1,2-isothiazolidine-1,1-dioxide (10a)

According to a similar method as that of Example 1, an aldol reaction was carried out using compound 6 and N-(tert-butoxycarbonyl)-1,2-isothiazolidine-1,1-dioxide 4o, which had been prepared from starting materials,3-chloropropylsulfonyl chloride and tert-butyl carbonate, in accordance with the method of reaction scheme 1, to give a crude addition compound 7o. To a solution of the crude addition compound 7o in toluene was added p-toluenesulfonic acid hydrate and the resultant mixture was heated to reflux for 45 minutes and then subjected to column chromatography on silica gel. From the fraction eluted with a mixture of n-hexane/ethyl acetate (2:1), the objective compound 10a (yield 8.5%) was obtained.

M.p.=233°-234° C.
IR(CHCl₃)cm⁻¹:3618,2952,1435,1366,1311,1240,1155,1070.
NMR(CDCl₃)δ:1.45(18H,s,2×Buᵗ),3.18(2H,dt,J=2.-6,6.8Hz,CH₂), 3.42-3.60(2H,m,CH₂),4.05-4.25(1H,- similar to that described in Example 8 in toluene (150 ml) was added p-toluenesulfonic acid hydrate (1.3 g). The resultant mixture was heated to reflux for 30 minutes and filtered through a small amount of silica gel. The filtrate was distilled to remove the solvent to give a mixture of crude (E)- and (Z)-2-(4-methoxybenzyl)-5-(3,5-di-tert-butyl-4-hydroxy)benzylidene-1,2-isothiazol 1,1-dioxides 8h and 9h (8.83 g). To a solution of the mixture in methylene chloride (150 ml) was added titanium tetrachloride (4.1 ml). The resultant mixture was stirred for 30 minutes at 0° C. and then subjected to column chromatography on silica gel. From the fraction eluted with a mixture of n-hexane/ethyl acetate (1:1), compounds 10a (3.35 g,41%) and 10b (120 mg,1.5%) were obtained. Physicochemical data of compound 10a agreed with those of the authentic sample obtained in Example 15.

Compound 10b: m.p.=161°-164° C.
IR(CHCl₃)cm⁻¹:
3620,2954,1432,1371,1312,1241,1157.
NMR(CDCl₃)δ:1.45(18H,s,2×Buᵗ),3.11(2H,dt,J=2.-1,6.7Hz,CH₂), 3.39-3.51(2H,m,CH₂),4.26-4.40(1H,- broad,NH),5.49(1H,s,OH),
6.80(1H,t,J=2.1Hz,CH),7.55(2H,s,2×aromatic-H).

Elementary analysis($C_{18}H_{27}NO_3S$)
Calcd:C,63.72;H,8.08;N,4.13;S,9.45
Found:C,63.64;H,8.14;N,4.06;S,9.36.

Example 17 ($R^3$ =H) (Y =3,4-dimethoxybenzyl)

To a solution of the addition compound 7i (4.0 g, 7.3 mmol) of the aldol reaction obtained in Example 9 in xylene (50 ml) were added an equimolar amount of each of 2,6-di-tert-butylphenol, anisole and p-toluenesulfonic acid hydrate. The resultant mixture was heated to reflux for 45 minutes and subjected to column chromatography on silica gel to give compounds 10a (580 mg,24%) and 10b (85–3.5%). Physicochemical data of compounds 10a and 10b agreed with those of authentic samples obtained in Examples 15 and 16, respectively.

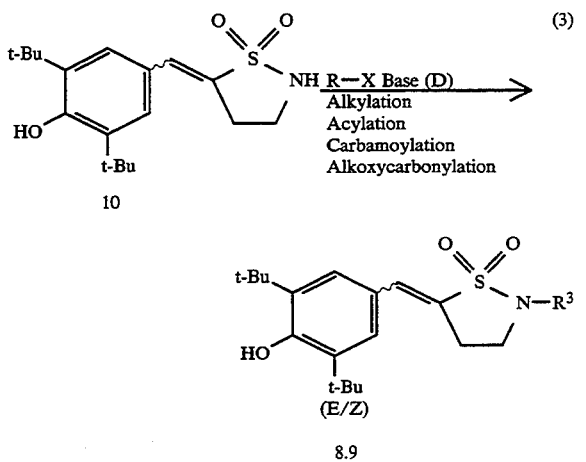

Example 18 ($R^3$=$CH_2CO_2C_2H_5$)

(E)-2-Ethoxycarbonylmethyl-5-(3,5di-tert-butyl-4-hydroxy) benzylidene-1,2-isothiazolidine-1,1-dioxide (8p)

(E)-5-(3,5-Di-tert-butyl-4-hydroxy) benzylidene1,2-isothiazolidine-1,1-dioxide 10a (500 mg,1.48 mmol), ethyl iodoacetate (240 μl, 2 mmol), an aqueous solution of 2N sodium hydroxide (1.5 ml,3 mmol) and a small amount of N-benzyltrimethylammonium chloride were added in turn to a mixture of chloroform (20 ml) and water (10 ml). The resultant mixture was stirred for 24 hours at room temperature and then treated in a conventional manner. The product was purified by column chromatography on silica gel to give 300 mg (49%) of the objective compound 8p.

IR(CHCl$_3$)cm$^{-1}$:3620,2956,1747,1435,1298,1229,1160.
NMR(CDCl$_3$)δ:1.29 (3H,t,J=7.2Hz,CH$_3$),1.45(18H,s,2×Bu$^t$), 3.19 (2H, dt,J=2.6,6.6Hz, CH$_2$ ),3.51 (2H,t, J=6.6Hz, CH$_2$),3.87 (2H,s,CH$_2$CO),4.23(2H,q,J=7.2Hz,CH$_2$),5.52(1H,s,OH),7.22–7.30 (3H,m,2×aromatic-H,CH).

Example 19 ($R^3$=$CH_2COOH$)

(E)-2-Carboxymethyl-5-(3,5-di-tert-butyl-4-hydroxy) benzylidene-1,2-isothiazolidine-1,1-dioxide (8q)

Compound 8p (610 mg,1.44 mmol) as obtained in a similar manner as that described in Example 18 and an aqueous solution of 2N-sodium hydroxide (1.5 ml) were added to a mixture of THF (10 ml) and methanol (4 ml). The resultant mixture was stirred at 0° C. for 30 minutes. After the addition of ethyl acetate (50 ml), the reaction mixture was washed with an aqueous solution of 1N hydrochloric acid (20 ml) and a saturated brine (20 ml), dried over anhydrous sodium sulfate and distilled in vacuo to remove the solvent to give 445 mg (78%) of the objective compound 8q (m.p=175°–178° C.).

IR(CHCl$_3$)cm$^{-1}$:3620,2954, 1735,1435,1297,1240, 1149.
NMR(CDCl$_3$)δ:1.45(18H,s,2×Bu$^t$),3.20 (2H,dt,J=2.6,6.6Hz, CH$_2$),3.51(2H,t,J=6.6Hz, CH$_2$),3.95(2H,s,CH$_2$CO),5.54(1H,s,OH), 7.25(2H, s,2×aromatic-H).

Elementary analysis($C_{20}H_{29}NO_5S$)
Calcd:C,60.46;H,7.41;N,3.53;S,8.07
Found:C,60.34;H,7.40;N,3.56;S,8.04.

Example 20 ($R^3$=$CH_2CH_2OH$)

(E)-2-(2-Hydroxyethyl)-5-(3,5-di-tert-butyl-4-hydroxy) benzylidene-1,2-isothiazolidine-1.1-dioxide (8r)

Compound 10a (675 mg,2 mmol),2-iodoethanol (624 μl, 8 mmol), an aqueous solution of 2N-sodium hydroxide (2 ml) and a small amount of N-benzyltrimethylammonium chloride were added to a mixture of methylene chloride (20 ml) and water (10 ml). The resultant mixture was heated to reflux for 3 days and treated in a conventional manner and the product was subjected to column chromatography on silica gel. From the fraction eluted with a mixture of n-hexane/ethyl acetate (7:3),190 mg (25%) of the objective compound 8r (m.p.=156°–157° C.) was obtained.

IR(CHCl$_3$)cm$^{-1}$:3620,2950,1434,1290,1240,1151,1066.
NMR(CDCl$_3$)δ:1.45(18H,s,2×Bu$^t$),3.16 (2H,dt,J=2.4, 6.5Hz,CH$_2$), 3.30(2H,m,CH$_2$),3.41 (2H,t,J=6.5Hz, CH$_2$),3.87 (2H,t,J=5.2Hz), 5.53 (1H,s,OH),7.23–7.29(3H,m,2×aromatic-H,CH).

Elementary analysis ($C_{20}H_{31}NO_4S$)
Calcd:C,62.96;H,8.19;N,3.67;S,8.40.
Found:C,62.72;H,8.27;N,3.69;S,8.21.

Example 21 ($R^3$ =$CH_2N(CH_3)_2$)

(E)-2-(2-Dimethylamino)ethyl)-5-(3,5-di-tert-butyl-4-hydroxy) benzylidene-1,2-isothiazolidine-1,1-dioxide (8s )

Compound 10a (843 mg,2.5 mmol ), N, N-dimethyl-2-bromoethylamine (750 mg,5 mmol ), an aqueous solution of 2N-sodium hydroxide (3 ml,6 mmol) and a small amount of N-benzyltrimethylammonium chloride were added to a mixture of chloroform (30 ml ) and water (10 ml ). The resultant mixture was stirred for 2 hours under ice-cooling. The chloroform layer was washed with water (20 ml×2) and dried over anhydrous sodium sulfate. The solution was distilled in vacuo to remove chloroform to give 950 mg (93%) of the objective compound as a crystalline residue (m.p.=160°–165° C.).

IR(CHCl$_3$)cm$^{-1}$:3620,2956,1435,1290, 1148.
NMR(CDCl$_3$)δ:1.45(18H,s,2×Bu$^t$),2.29 (6H,s,N(CH$_3$)2),2.60 (2H,t,J=6.6Hz,CH$_2$),3.12(2H,dt,J=2.2,6.6Hz,CH$_2$),3.-20(2H,t, J=6.6Hz,CH$_2$),3.38(2H,t,J=6.6Hz,CH$_2$),5.51(1H,s,OH),7.21–7.28 (3H,m,2×aromatic-H,CH).

Elementary analysis($C_{22}H_{36}N_2O_3S\times0.2CH_2Cl_2$)
Calcd:C,62.65;H,8.62;N,6.58;S,7.53;Cl,3.33

Found:C,62.32;H,8.60;N,6.71;S,7.56;Cl,3.24.

Example 22 ($R^3$=COCH3)

(E)-2-Acetyl-5-(3,5-di-tert-butyl-4-hydroxy)benzylidene-1,2-isothiazolidine-1,1-dioxide (8t)

To a solution of compound 10a (585 mg,1.74 mmol) in pyridine (10 ml) and a small amount of 4-N,N-dimethylaminopyridine, acetic anhydride (6 ml) was added dropwise under ice-cooling. The resultant mixture was stirred for 1 hour at room temperature and concentrated in vacuo. The residue was dissolved in ethyl acetate and the solution was filtered through a small amount of silica gel. The filtrate was concentrated in vacuo to give 360 mg (55%) of the objective compound as a crystal-like residue (m.p.=177°-179° C. ).

IR(CHCl3)cm$^{-1}$:3618,2958,1695,1435,1379,1297,1153,1117.

NMR(CDCl3)δ:1.46(18H,s,2×Bu$^t$), 2.53(3H,s,COCH3), 3.20 (2H,dt,J=2.2,7.0Hz,CH2),3.86(2H,t,J=7.0Hz,CH2),5.60(1H,s, OH),7.52(2H,s,2×aromatic-H),7.39(1H,t,j=2.2Hz,CH).

Elementary analysis($C_{20}H_{29}NO_4S$)
Calcd:C,63.30;H,7.70;N,3.69;S,8.45
Found:C,63.27;H,7.83;N,3.64;S,8.22.

Example 23 ($R^3$ =N-methyl-N-methoxy)

(E)-2-(N-Methyl-N-methoxy)carbamoyl-5-(3,5-di-tert-butyl-4-hYdroxy)benzylidene-1,2-isothiazolidine-1,1-dioxide (8u)

Compound 10a (450 mg,1.33 mmol) and N-methyl-N-methoxy-O-phenyl carbamate (300 mg,1.66 mmol) were dissolved in a mixture of THF (10 ml) and HMPA (10 ml).

To the solution was added dropwise a solution of lithium hexamethyldisilazane (LiHMDS) in THF (1 M,3.2 ml) with stirring and cooling to −40° C. After the reaction solution was warmed to room temperature, it was poured into an aqueous solution of 1N hydrochloric acid (20 ml). The mixture was then extracted with ethyl acetate (30 ml). The ethyl acetate layer was washed with water (30 ml) and a saturated brine (30 ml), dried over anhydrous sodium sulfate and distilled in vacuo to remove the solvent. The residue was subjected to column chromatography on silica gel. From the fraction eluted with a mixture of n-hexane/ethyl acetate (7:3), the objective compound 8u (230 mg,41%) was obtained.

IR(CHCl3)cm$^{-1}$:3620,2958,1673,1435,1388,1330,1240,1207, 1155,1092.

NMR(CDCl3)δ:1.45(18H,s,2×Bu$^t$),3.21(2H,dt,j=2.2,6.8Hz,CH2), 3.31(3H,s,NCH3),3.78(3H,s,OCH3),3.89(2H,t,j=6.8Hz),5.54 (1H,s,OH),7.23(2H,s,2×aromatic-H),7.31(1H,t,j=2.2Hz,CH).

Example 24 ($R^3$ =N-benzylozy-N-methoxymethyl)

(E)-2-(N-Benzyloxyl-N-methoxymethyl)carbamoyl-5-(3,5-di-tert-butyl-4-hydroxy)benzylidene-1,2-isothiazolidine-1,1-dioxide (8v)

Compound 10a (424 mg,1.26 mmol) and N-benzyloxy-N-methoxymethyl-O-phenyl carbamate (722 mg,2.52 mmol) in a mixture of THF (90 ml) and HMPA (300 ml) were treated with a solution of LiHMDS in THF (1 M,4.0 ml) in a manner similar to that described in Example 23. The reaction product was subjected to column chromatography on silica gel. From the fraction eluted with a mixture of n-hexane/ethyl acetate (3:1) the objective compound 8v (600 mg,90%) was obtained.

NMR(CDCl3)δ:1.45(18H,s,2×Bu$^t$),3.18(2H,dt,J=2.0,6.8Hz,CH2), 3.45(3H,s,OCH3),3.79(2H,t,J=6.8Hz,CH2),4.94(2H,s,OCH2),5.02 (2H,s,OCH2),5.54(1H,s,OH),7.22(2H,s,2×aromatic-H),7.30(1H,t, J=2.0Hz,CH),7.30-7.55(5H,m,5×aromatic-H).

Example 25 ($R^3$=CONHOH)

(E)-2-(Hydroxycarbamoyl)-5-(3,5-di-tert-butyl-4-hydroxy) benzylidene-1.2-isothiazolidine-1,1-dioxide (8w)

To a solution of compound 8v (600 mg,1.13 mmol) obtained in Example 24 in methylene chloride (8 ml) was added titanium tetrachloride (500 μl,4.56 mmol) under icecooling and the resultant mixture was stirred for 1.5 hours. After the addition of an aqueous solution of 2N hydrochloric acid (10 ml), the reaction mixture was stirred for 30 minutes at room temperature and then extracted with methylene chloride (20 ml). The organic layer was washed with a saturated brine (20 ml), dried over anhydrous sodium sulfate and distilled in vacuo to remove the solvent. The residue was subjected to column chromatography on silica gel. From the fraction eluted with a mixture of n-hexane/ethyl acetate (1:1 ), the objective compound 8w (150 mg,33% ) was obtained.

IR(CHCl3)cm$^{-1}$:3618,2956,1707,1434,1320,1151,1100.

NMR(CDCl3)δ:1.45 (18H,s,2×Bu$^t$),3.23(2H,dt,J=2.2,7.0Hz,CH2), 3.94(2H,t,J=7.0Hz,CH2),5.61(1H,s,OH),6.85-6.95(1H,broad,OH ),7.24(2H,s,2×aromatic-H ),7.30(1H,t, J=2.2Hz, CH),8.61(1H,s,NH).

Example 26

(E)-2-Hydroxy-5-(3,5-di-tert-butyl-4-hydroxy)benzylidene-1,2-isothiazolidine-1,1-dioxide (11a) and its (Z)-isomer (11b)

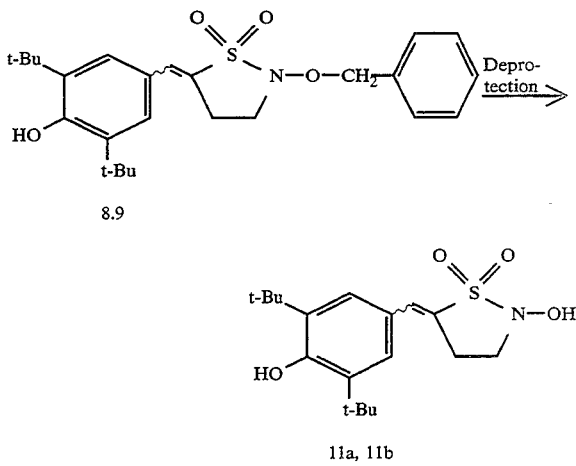

8.9

11a, 11b

According to Example 1, an aldol reaction was carried out using compound 6a and N-benzyloxy-1,2-isothiazolidine-1,1-dioxide. The addition compound obtained by the aldol reaction was treated with p-toluenesulfonic acid hydrate to give crude 2-benzyloxy-5(3,5- di-tert-butyl-4-hydroxy) benzylidene-1,2-isothiazolidine-1,1-dioxide. To a solution of the crude dioxide (4.44 g,10 mmol) in methylene chloride (80 ml) was added dropwise titanium tetrachloride (4.4 ml,40 mmol) with stirring and ice-cooling. After stirring for another 2 hours at the same temperature, an aqueous solution of 1N hydrochloric acid (50 ml) was added to the reaction mixture. The methylene chloride layer was separated, washed with water (50 ml) and a saturated brine (50 ml), dried over anhydrous sodium sulfate and distilled in vacuo to remove the solvent. The residue was subjected to column chromatography on silica gel. From the fraction eluted with a mixture of n-hexane/ethyl acetate (3:1), the objective compounds 11b (178 mg,5%) and 11a (1.6 g,45%) were obtained in turn.

Compound 11a: m.p.=177°–182° C. (decomp.)
IR(KBr)cm$^{-1}$:3560,3430,1425,1330,1240,1155,1130,-1115.
NMR(CDCl$_3$)δ:1.45(18H,s,2×But),3.18(2H,dt,J=2.-6,6.8HzCH$_2$), 3.89(2H,t,J=6.8Hz,CH$_2$),5.56(1H, s,OH),6.18–6.30(1H,broad,OH),7.26–7.35(3H,m,-2×aromatic-H,CH).
Elementary analysis(C$_{18}$H$_{27}$NO$_4$S)
Calcd:C,61.16;H,7.70;N,3.96;S,9.07
Found:C,60.86;H,7.68;N,3.93;S,8.90.

Compound 11b: m.p.=190 –198° C. (decomp.)
IR(CHCl$_3$)cm$^{-1}$:3622,3540,3020, 2954, 1632,1431,1340, 1241,1157.
NMR(CDCl$_3$) δ:1.45 (18H,s,2×Bu$^t$),3.17(2H,dr, J=2.2,6.8Hz,CH$_2$), 3.62(2H,m,CH$_2$),5.51(1H,s,OH),6.22(1H,-s,OH)7.04(1H,t, J=2.2Hz, CH ),7.49 (2H,s,2×aromatic-H).
Elementary analysis(C$_{18}$H$_{27}$NO$_4$S)
Calcd:C,60.16;H,7.70;N,3.96; S,9.07
Found:C,60.67;H,7.58;N,3.96; S,8.87.

Example 27

(E)-2-Isopropyl-5-(3,5-di-tert-butyl-4-hydroxy) benzylidene-1,2-isothiazolidine-1,1-dioxide (8x)

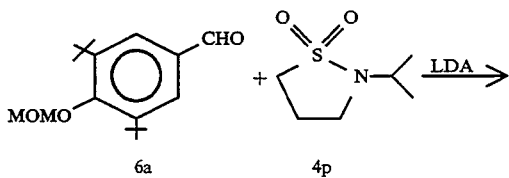

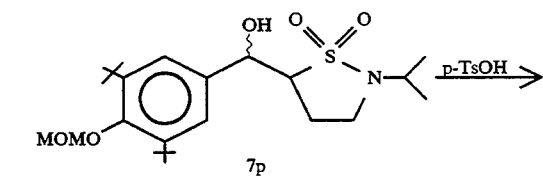

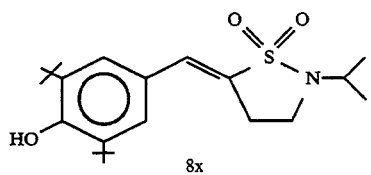

According to a similar method as that of Example 1, an aldol reaction was carried out using N-isopropyl-1,2-isothiazolidine-1,1-dioxide (4p) (3.65 g,22.4 mmol) and 3,5-di-tert-butyl-4-methoxymethoxybenzaldehyde (6a) (5.28 g,19.0 mmol) to give 6.27 g (74.7%) of addition compound (7p) as a white powder. To a solution of the addition compound 7p (6.27 g) in toluene (120 ml) was added p-toluenesulfonic acid hydrate (600 mg). The mixture was heated to reflux for 30 minutes, cooled, washed twice with water (100 ml), dried over anhydrous sodium sulfate and distilled in vacuo to remove the solvent. The crystalline residue was recrystallized from methanol to give 2.16 g (30%) of the objective compound as colorless crystals.

Compound 8x: m.p.=148°–150° C.
IR(KBr)cm$^{-1}$:3550, 2960, 1645, 1600, 1432, 1273, 1173.
NMR(CDCl$_3$)δ:1.29(6H,d,J=6.6 Hz,2×CH$_3$),1.45(18H,s,2×Bu$^t$),3.-07–3.14(2H,m,CH$_2$),3.29–3.35(2H,m,CH$_2$), 3.94(1H, sept,CH),5.48(1H,s,OH),7.22(1H,t,J=2.8 Hz, CH),7.23(2H, s, Ar-H).
Elementary analysis(C$_{21}$H$_{33}$NO$_3$S)
Calcd:C,66.45;H,8.76;N,3.69;S,8.45
Found:C,66.37;H,9.01;N,3.67;S,8.28.

Example 28

(E)-2-Ethyl-5-(3,5-dimethyl-4,hydroXy)benzylidene-1,2-isothiazolidine-1,1dioxide (8y)

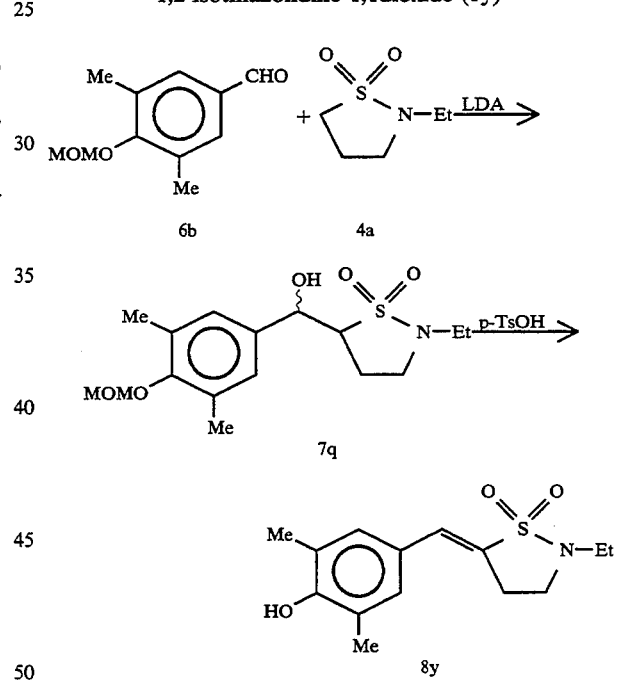

According to a similar method as that of Example 1, an aldol reaction was carried out using N-ethyl-1,2-isothiazolidine-1,1-dioxide (4a) (2.5 g,16.8 mmol) and 3,5-dimethyl-4-methoxymethoxybenzaldehyde (6b) (2.92 g,15 mmol) to give 4.01 g (77.8%) of addition compound (7q) as a white powder. To a solution of the aldol addition compound 7q (3.75 g,10.9 mmol) in toluene (100 ml) was added p-toluenesulfonic acid hydrate (200 mg). The mixture was heated to reflux for 30 minutes. The reaction mixture was cooled, washed twice with water (100 ml), dried over anhydrous sodium sulfate and distilled in vacuo to remove the solvent. The crystalline residue was recrystallized from methanol to give 1.63 g (53%) of the objective compound as colorless crystals.

Compound 8y:m.p.=167°–168° C.

IR(Nujol)cm$^{-1}$:3399, 1641, 1593, 1489, 1461, 1272, 1217, 1170, 1145, 1128.

NMR(CDCl$_3$)δ:1.29(3H,t,J=7.4 Hz,CH$_3$),2.26(6H,s,2 ×CH$_3$),3.05–3.36(6H,m,2×CH$_2$, NCH$_2$),5.00(1H, broad, OH),7.04(2H, s, Ar-H),7.15(1H, t, J=2.8 Hz, CH).

Elementary analysis (C$_{14}$H$_{19}$NO$_3$S)
Calcd:C,59.76;H,6.81;N,4.98;S,11.39
Found:C,59.56;H,6.85;N,4.99;S,11.38.

Example 29

(E)-2-Ethyl-5-(3,5-diisopropyl-4-hydroxy)benzylidene-1,2-isothiazolidine-1,1-dioxide (8z)

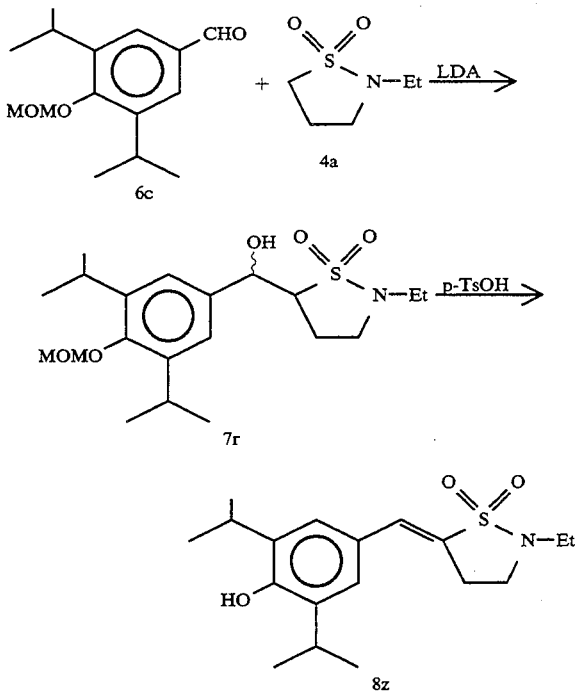

According to a similar method as that of Example 1, an aldol reaction was carried out using N-ethyl-1,2-isothiazolidine-1,1-dioxide (4a) (4.9 g,32.8 mmol) a 3,5-diisopropyl-4-methoxymethoxybenzaldehyde (6c) (7.51 g, mmol) to give 6.07 g (50.6%) of addition compound (7r) as a white powder. To a solution of the aldol addition compound 7r (5.0 g,20 mmol) in toluene (100 ml) was added p-toluenesulfonic acid hydrate (200 mg). The mixture was heated to reflux for 30 minutes. The reaction mixture was cooled, washed twice with water (100 ml), dried over anhydrous sodium sulfate and distilled in vacuo to remove the solvent. The crystalline residue was recrystallized from methanol to give 3.24 g (48%) of the objective compound 8z as colorless crystals.

Compound 8z: m.p.=167°–168° C.
IR(Nujol)cm$^{-1}$:3413, 1644, 1600, 1472, 1276, 1194, 1153 1115.

NMR(CDCl$_3$)δ:1.27(12H,d,J=6.6 Hz,2×CH(CH$_3$)$_2$),3.06–3.36(8H,m,3×CH$_2$,2×CH),5.-13(1H,s,OH),7.12(2H,s, Ar-H),7.24(1H, t, J=2.8 Hz, CH).

Elementary analysis(C$_{18}$H$_{27}$NO$_3$S)
Calcd:C,64.06;H,8.07;N,4.15;S,9.50
Found:C,64.03;H,8.02;N,4.11;S,9.46.

Example 30

(E)-2-Ethyl-5-(3,5-dimethoxy-4-hydroxy)benzylidene-1,2-isothiazolidine-1,1dioxide (8Ia)

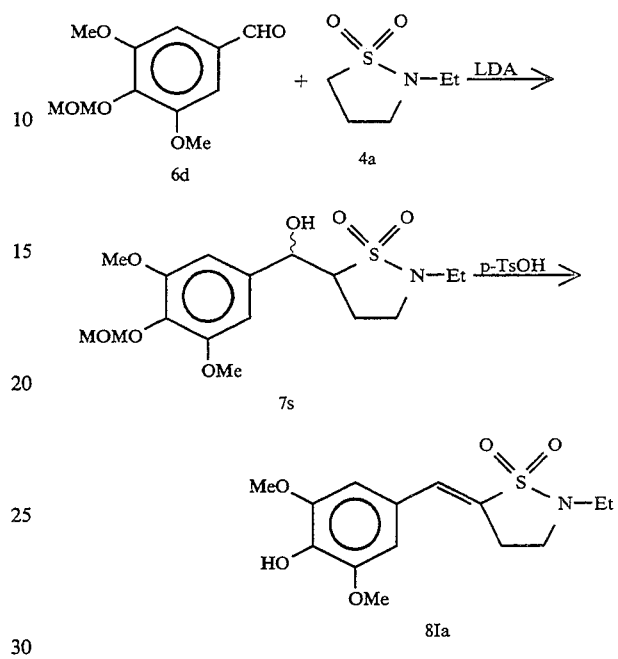

According to a similar method as that of Example 1, an aldol reaction was carried out using N-ethyl-1,2-isothiazolidine-1,1-dioxide (4a) (5.22 g,35 mmol) and 3,5-dimethoxy-4-methoxymethoxybenzaldehyde (6d) (6.77 g,30 mmol) to give 8.42 g (74.8%) of addition compound 7s as a white powder. To a solution of the aldol addition compound 7s (4.28 g,11.4 mmol) in toluene (100 ml) was added ptoluenesulfonic acid hydrate (200 mg). The mixture was heated to reflux for 30 minutes. The reaction mixture was cooled, washed twice with water (100 ml), dried over anhydrous sodium sulfate and distilled in vacuo to remove the solvent. The resulting crystalline residue was recrystallized from methanol to give 1.64 g (46%) of the objective compound 8Ia as colorless needle crystals.

Compound 8Ia: m.p.=164°–166° C.
IR(Nujol)cm$^{-1}$:3434, 1643, 1607, 1593, 1517, 1454, 1321, 1273, 1251, 1219, 1172, 1149, 1109.
NMR(CDCl$_3$)δ:1.30(3H, t, J=7.4 Hz, CH$_3$),3.10–3.37(6H,m,3×CH$_2$),3.92(6H, s,2 ×OCH$_3$),5.76(1H,s,OH),6.65(2H, s, Ar-H ),7.20 (1H, t, J=2.8 Hz, CH ).

Elementary analysis (C$_{14}$H$_{19}$NO$_5$S)
Calcd:C,53.66;H,6.11;N,4.47;S,10.23
Found:C,53.45;H,6.06;N,4.44;S,10.33.

Example 31

(E)-2-Ethyl-5-(3-methoxy-4-hydroxy)benzylidene-1,2-isothiazolidine-1,1-dioxide (8Ib)

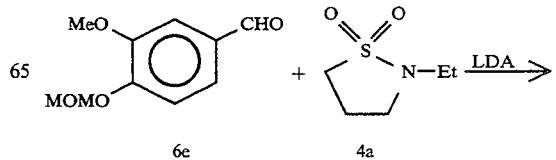

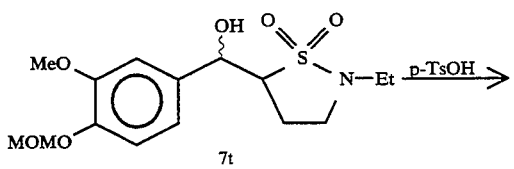

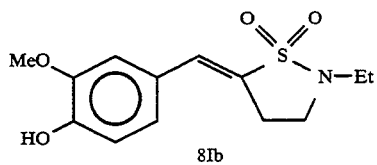

According to a similar method as that of Example 1, an aldol reaction was carried out using N-ethyl-1,2-isothiazolidine-1,1-dioxide 4a (5.00 g,33.5 mmol) with 3-methoxy-4-methoxymethoxybenzaldehyde (6e) (5.88 g,30 mmol) to give 4.35 g (42%) of addition compound 7t as a white powder. To a solution of the aldol addition compound 7t (4.30 g,12.4 mmol) in toluene (100 ml) was added p-toluenesulfonic acid hydrate (200 mg). The mixture was heated to reflux for 30 minutes. The reaction mixture was cooled, washed twice with water (200 ml), dried over anhydrous sodium sulfate and concentrated in vacuo. The residue was subjected to column chromatography on silica gel. The fraction eluted with n-hexane:ethyl acetate (2:1) was isolated and recrystallized from a mixture of methylene chloride/diisopropyl ether to give 2.7 g (31.8%) of the objective compound as colorless crystals.

Compound 8Ib: m.p.=146°-148° C.

IR(Nujol)cm$^{-1}$:3404, 2924, 1646, 1611, 1594, 1516, 1462, 1270, 1149, 1130.

NMR(CDCl$_3$)δ:1.29(JH, t, J=7.4 Hz, CH$_3$),3.8-3.18(2H, m, CH$_2$),3.17(2H, q, J=7.4 Hz,2×CH$_2$),3.26-3.34(2H, m, CH$_2$),3.92(3H,s, OCH$_3$),5.88(1H, s, OH),6.86-7.02(3H, m, Ar-H),7.21(1H, t, J=2.8 Hz, CH).

Elementary analysis (C$_{13}$H$_{17}$NO$_4$S)
Calcd:C,55.11;H,6.05;N,4.94;S,11.32
Found:C,54.75;H,6.11;N,4.99;S,11.23.

Example 32

(E)-2-Ethyl-5-(4-hydroxy)benzylidene-1,2-isothiazolidine-1,1-dioxide (8Ic)

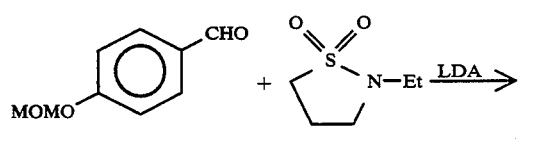

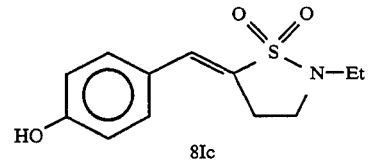

According to a similar method as that of Example 1, an aldol reaction was carried out using N-ethyl-1,2-isothiazolidine-1,1-dioxide 4a (3.28 g,22 mmol) with 4-methoxymethoxybenzaldehyde (6f) (3.32 g,20 mmol) to give 4.10 g (65%) of addition compound 7u as a white powder. To a solution of the aldol addition compound 7u (4.00 g,12.7 mmol) in toluene (100 ml) was added p-toluenesulfonic acid hydrate (200 mg). The mixture was heated to reflux for 30 minutes. The reaction mixture was washed twice with water (200 ml), dried over anhydrous sodium sulfate and concentrated in vacuo. The residue was subjected to column chromatography on silica gel. The fraction eluted with n-hexane/ethyl acetate (3:2) was isolated and recrystallized from a mixture of methylene chloride and diisopropyl ether to give 1.0 g (31.1%) of the objective compound as colorless crystals.

Compound 8Ic: m.p.=135°-138° C.

IR(Nujol)cm$^{-1}$:3346, 2914, 1646, 1605, 1584, 1513, 1453, 1376, 1282, 1223, 1136.

NMR(CDCl$_3$)δ:1.29(3H, t, J=7.2 Hz, CH$_3$),3.04-3.12(2H, m, CH$_2$),3.17(2H, q, J=7.2 Hz, CH$_2$),3.27-3.33(2H, m, CH$_2$), 5.59(1H, s, OH),6.85-6.90(2H, m, Ar-H),7.19(1H, t, J=2.8 Hz, CH),7.24-7.30(4H, m, Ar-H).

Elementary analysis(C$_{12}$H$_{15}$NO$_3$S)
Calcd:C,56.90;H,5.97;N,5.53;S,12.66
Found:C,56.74;H,5.98;N,5.52;S,12.41.

Example 33

(E)-2-(3,5-Di-tert-butyl-4-hydroxy)benzylidene-sulfolane (8Id)

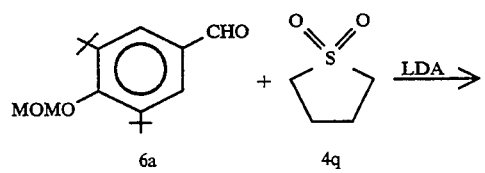

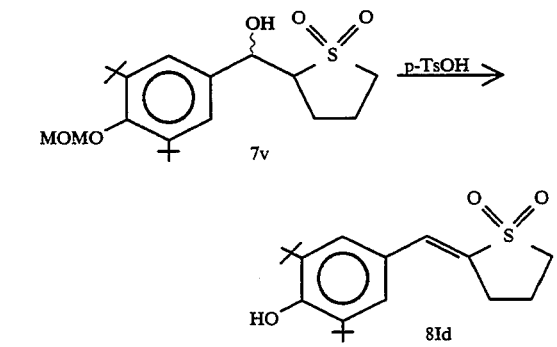

According to a similar method as that of Example 1, an aldol reaction was carried out using sulfolane 4q (2.4 g,20 mmol) and 3,5-di-tert-butyl-4-methoxymethoxybenzaldehyde 6a (5.57 g,20 mmol) to give 5.58 g (70%) of addition compound 7v as a white powder. To a solution of the aldol addition compound 7v (4.00 g,10.0 mmol) in toluene (100 ml) was added p-toluenesulfonic acid hydrate (200 mg). The mixture was heated to reflux for 30 minutes. The reaction mixture was washed twice with water (200 ml), dried over anhydrous sodium sulfate and concentrated in vacuo. The resulting residue was subjected to column chromatography on silica gel and the fraction eluted with n-hexane/ethyl acetate (3:1) was collected, concentrated in vacuo and recrystallized from a mixture of n-hexane:ether to give 1.346 g (40%) of the objective compound as colorless crystals.

Compound 8Id: m.p.=152°–154° C.

IR(Nujol)cm$^{-1}$:3608, 2914, 1638, 1597, 1461, 1376, 1285, 1214, 1133.

NMR(CDCl$_3$)δ:1.45(18H, s,2×Bu$^t$),2.31(2H, q, J=7 Hz, CH$_2$), 3.00–3.07(4H, m,2 ×CH$_2$),5.51(1H, s, OH),7.22(1H, t, J=2.6Hz, CH ),7.26 (2H, s, Ar-H ).

Elementary analysis (C$_{19}$H$_{28}$O$_3$S)
Calcd:C,67.82;H,8.38;S,9.53
Found:C,67.90;H,8.38;S,9.34.

Example 34

(E)-6-(3,5-Di-tert-butyl-4-hydroxy) benzylidene-2-methyl-4,5-dihydro-6H-1,3,2-thiaoxazine-1,1-dioxide (8Ie)

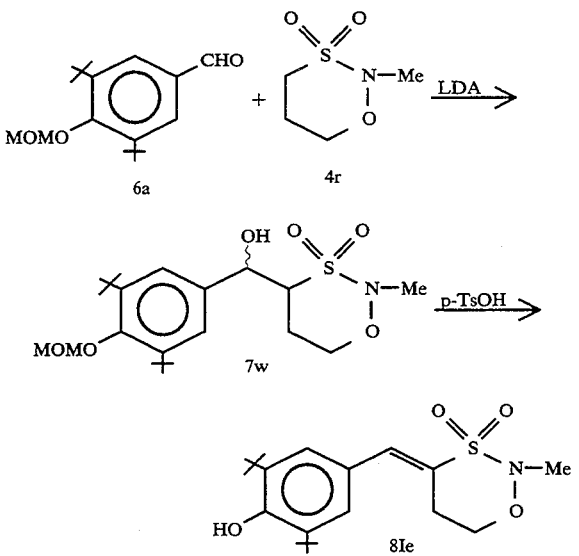

According to a similar method as that of Example 1, an aldol reaction was carried out using N-methyl-1,3,2-thiaoxazine-1,1-dioxide 4r (575 mg,3.80 mmol) and tert-butyl-4-methoxymethoxybenzaldehyde 6a (846 mg,304 mmol) to give 1,458 g of addition compound 7w as a white powder. To a solution of the aldol addition compound 7w (1,458 g) in toluene (50 ml) was added p-toluenesulfonic acid hydrate (150 mg). The mixture was heated to reflux for 30 minutes. The reaction product was subjected to column chromatography on silica gel and the fraction eluted with a mixture of n-hexane/ethyl acetate (6:1) the objective compound (511 mg,43%) was obtained as colorless crystals.

Compound 8Ie: m.p.=215°–216.5° C.

IR(KBr)cm$^{-1}$:3599, 3438, 2960, 1637, 1599, 1437, 1326, 1298, 1153.

NMR(CDCl$_3$)δ:1.44(18H. s,2 ×Bu$^t$),3.00(3H,s, CH$_3$),3.26–3.32(2H, m, CH2),4.12–4.17(2H, m, CH$_2$),5.49(1H, s, OH), 7.15(2H, s, Ar-H),7.55(1H, broad, CH).

Elementary analysis (C$_{19}$H$_{29}$NO$_4$S)
Calcd:C,62.10;H,7.95;N,3.81;S,8.72
Found:C,62.03;H,7.91;N,3.92;S,8.51.

Example 35

(E)-6-(3,5-Di-tert-butyl-4-hydroxy) benzylidene-2-methoxy-3,4,5,6-tetrahydro-1,2-thiazine-1,1-dioxide (8If)

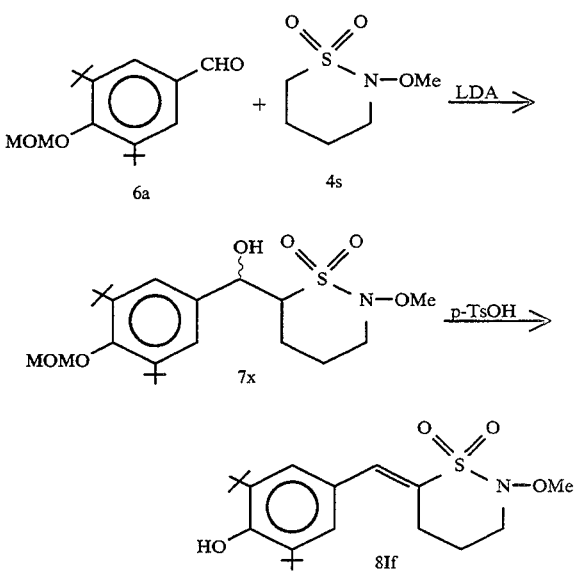

According to a similar method as that of Example an aldol reaction was carried out using N-methoxy-3,4,5,6-tetrahydro-1,2-thiazine-1,1-dioxide 4s (2.73 mg, 16.5 mmol) and 3,5-di-tert-butyl-4-methoxymethoxybenzaldehyde 6a (5.0 g,18 mmol) to give 7.3 g of addition compound 7x. To a solution of the aldol addition compound 7x (2.1 g,4.73 mmol) in toluene (100 ml) was added p-toluenesulfonic acid hydrate (200 mg) and the mixture was heated to reflux for 30 minutes. The reaction product was subjected to column chromatography on silica gel and from the fraction eluted with n-hexane/ethyl acetate (4:1) the objective compound (750 mg,42) was obtained as a brown powder.

IR(CHCl$_3$)cm$^{-1}$:3618, 2950, 1630, 1435, 1340, 1238, 1161.

NMR(CDCl$_3$)δ:1.45(18H, s,2 ×Bu$^t$),1.80–1.95(2H, m, CH$_2$), 3.04(2H, t, J=6.0 Hz, CH2),3.77–3.83(2H, m, CH$_2$), 3.80(3H, s, OCH$_3$),5.46(1H, s, OH),7.20(2H, s, Ar-H), 7.46(1H, s, CH).

Example 36

(E)-5-(3,5-Di-tert-butyl-4-hydroxy) benzylidene-2-ethyl-1,2-isothiazolidine-3-one-1,1-dioxide (8Ig)

(1) (3,5-Di-tert-butyl-4-methoxymethoxybenzoyl)-N-ethyl-N-diphenylmethylmethanesulfonamide (14)

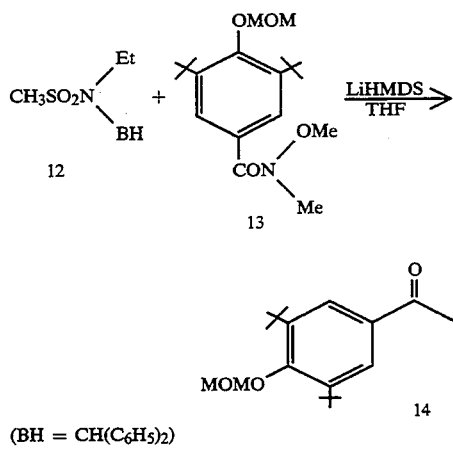

(BH = CH(C₆H₅)₂)

The compound (12) was synthesized in a conventional manner by reacting methanesulfonyl chloride with diphenylmethylamine in the presence of triethylamine followed by treating the resultant product with ethyl iodide in the presence of potassium carbonate. The compound (13) was prepared by converting 3,5-di-tert-butyl-4-hydroxybenzoic acid to an acid chloride in a conventional manner and reacting the acid chloride with N,O-dimethylhydroxylamine followed by methoxymethylation of the phenolic hydroxyl group.

A solution of compound (12) (16.82 g,58 mmol) in THF (200 ml) was cooled to below −50° C. To the solution was slowly added dropwise a solution of lithium bistrimethylsilylamide in THF (1.0 M) (64 ml,64 mmol) and the mixture was stirred for 30 minutes at −50° C. Subsequently, a solution of compound (13) (17.7 g,52.2 mmol) in THF (100 ml) was slowly added dropwise to the 10 mixture. After the reaction solution was warmed to room temperature, a saturated aqueous solution of ammonium chloride (500 ml) was added to it. The resultant mixture was extracted with ethyl acetate (400 ml). The organic layer was taken, washed with a saturated aqueous solution of sodium hydrogencarbonate (500 ml) and a saturated brine (500 ml), dried over anhydrous sodium sulfate and distilled in vacuo to remove the solvent. The residue was purified by column chromatography on silica gel eluting with nhexane/ethyl acetate (9:1 to 7:1) to give 27.2 g (92%) of compound 14 as a colorless oil.

IR(CHCl₃)cm⁻¹:2960,1673,1339,1188.

NMR( CDCl₃)δ:0.83 (3H, t, J=7.0Hz, CH₃),1.45 (18H, s,2×ᵗBu ), 3.56(2H, q, J=7.0Hz, CH₂),3.65(3H, s, CH₃),4.37(2H, s, CH₂ ),6.42(1H, s, CH ),7.31–7.38(10H, m,10×aromatic-H ),7.89 (2H, s, 2×aromatic-H).

(2) tert-Butyl 3-(3,5-di-tert-butyl-4-methoxymethoxybenzoyl)-3-(N-ethyl-N-diphenylmethylsulfamoyl) propionate (15)

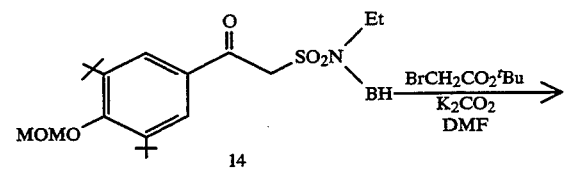

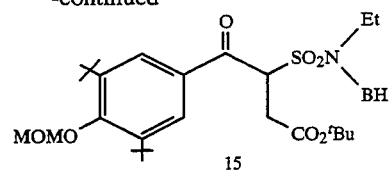

A suspension of (3,5-di-tert-butyl-4-methoxymethoxybenzoyl)-N-ethyl-N-diphenylmethylmethanesulfonamide (14) (27.0 g,47.7 mmol), tert-butyl bromoacetate (9.25 ml,57.3 mmol), and potassium carbonate (9.89 g,71.6 mmol) in DMF (300 ml) was stirred for 18 hours at room temperature. To the suspension was added water (600 ml) and the reaction mixture was extracted with ethyl acetate (800 ml). The organic layer was separated, washed with water (300 ml) and a saturated brine (500 ml), dried over anhydrous sodium sulfate and distilled in vacuo to remove the solvent. The resultant pale yellow solid, when washed well with n-hexane. and concentrated in vacuo gave 26.75 g (82%) of compound 15 as a colorless powder (m.p. =104°–105° C.).

IR(KBr)cm⁻¹:3435,1735,1677,1340,1164, 1147.

NMR( CDCl₃)δ:0.77(3H, t, J=7.0Hz, CH₃),1.21(9H, s, ᵗBu),1.44 (18H, S,2×ᵗBu),2.83(1H, dd, J=3.2,16.8Hz, CH₂×½),3.29–3.51 (3H, m, CH₂+CH₂×μ), 3.65 (3H, s, CH₃ ),4.90 (2H, s, CH₂),5.28 (1H,dd. J=3.2,10.4Hz,CH),6.39(1H, s,CH),7.31–7.34(10H,m,1-0×aromatic-H), 7.96(2H, s,2×aromatic-H).

Elementary analysis (C₃₉H₅₃NO₇S)
Calcd C,68.90;H,7.86;N,2.06;S,4.72
Found C,68.80;H,7.93;N,2.16;S,4.55.

(3 ) tert-butyl 4- (3,5-di-tert-butyl-4-methoxymethoxyphenyl)-4-hydroxy-3-(n-ethyl-N-diphenylmethylsulfamoyl)butyrate (16)

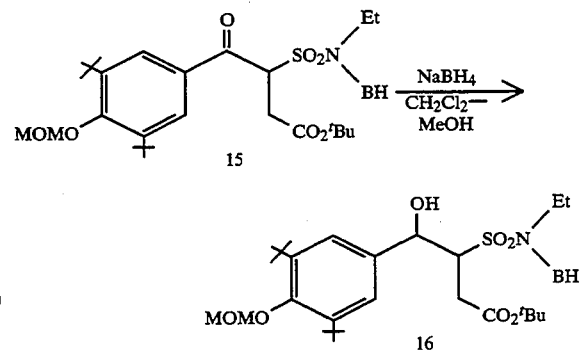

To a solution of tert-butyl 3-(3,5-di-tert-butyl-4-methoxymethoxybenzoyl)-3-(N-ethyl-N-diphenylmethylsulfamoyl) propionate (15) (22.6 g,33.2 mmol) in a mixture of MeOH (180 ml) and CH₂Cl₂ (180 ml) was added by portions sodium borohydride (1.89 g,49.9 mmol) under ice-cooling. The resultant mixture was warmed to room temperature and stirred for 45 minutes. To the mixture were then added acetone (5 ml) and saturated aqueous solution of ammonium chloride (400 ml) in turn and the reaction solution was extracted with methylene chloride (400 ml). The organic layer was separated, washed with water (400 ml) and a saturated brine (400 ml), dried over anhydrous sodium sulfate and distilled in vacuo to remove the solvent. The resultant pale pink solid, when washed well with n-hexane, gave 21.8 g (96%) of compound (16) as a colorless powder.

IR(KBr)cm$^{-1}$:3499,2970, 1737,1600,1319,1151.

NMR( CDCl$_3$)δ:0.84(3H, t, J=7.0Hz, CH$_3$ ),1.21 (9H, s, $^t$Bu ),1.41 (18H, S,2×$^t$Bu),2.22 (1H, dd, J=6.6,17.6Hz, CH$_2$×½),2.48 (1H, dd, J=4.2,17.6Hz, CH$_2$×½),3.37-3.58(2H, m, CH$_2$),3.62(3H, s, CH$_3$), 3.92-4.07 (1H, m, CH ),4.14 (1H, d, J=2.2Hz, OH ),4.86 (2H, s, CH$_2$), 4.97(1H,dd,J=2.2,9.2Hz,CH),6.47(1H, s,CH),7.19(2H, s, 2×aromatic-H),7.32-7.34(10H,m,1-0×aromatic-H).

Elementary analysis (C$_{39}$H$_{55}$NO$_7$S·0.7H$_2$O)
Calcd C,67.44;H,8.18;N,2.02;S,4.62
Found C,67.50;H,8.06;N,2.15;S,4.51.

(4) tert-Butyl 4-(3,5-di-tert-butyl-4-methoxy-methoxyphenyl)-4-hydroxy-3-(N-ethylsulfamoyl) butyrate (17)

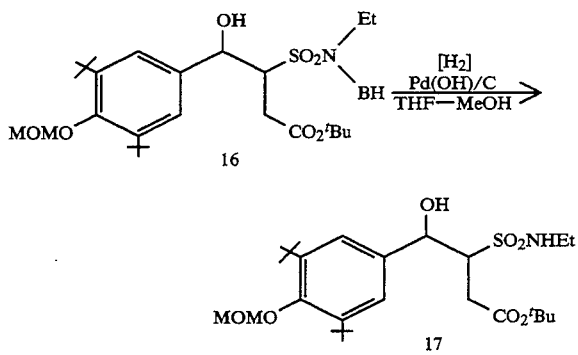

A suspension of tert-butyl 4-(3,5-di-tert-butyl-4-methoxymethoxyphenyl)-4-hydroxy-3-(N-ethyl-N-diphenylmethylsulfamoyl) butrate (16) (20.8 g,30.5 mmol) and palladium hydroxide on carbon (3.05 g) in a mixture of THF (100 ml) and methanol (200 ml) was stirred under hydrogen for 5 hours at room temperature. The catalyst was filtered off through celite and the filtrate was concentrated. The residue was recrystallized from ether-nhexane to obtain 13.69 g (87%) of compound (17) (m.p. =96°-97° C).

IR(KBr)cm$^{-1}$:3441,3298,2966,1736,1635,1367,1152.

NMR( CDCl$_3$)δ:1.15 (3H, t, J=7.4Hz, CH$_3$ ),1.36(9H, s, $^t$Bu ), 1.44(18H, S,2×$^t$Bu ),2.31 (1H, dd, J=5.6,17.6Hz, CH$_2$×½),2.80 (1H, dd, J-6.6,17.6Hz, CH$_2$×½),3.00-3.27(2H, m, CH$_2$),3.40 (1H,d,J=4-8Hz,OH),3.64(3H, s,CH$_3$),3.97(1H,ddd, J=5.6,6.6, 8.2Hz,CH),4.19-4.25(1H,m, NH),4.89(2H, s,CH$_2$),4.95(1H,dd, J=4.8,8.2Hz, CH ),7.27 (2H, s,2×aromatic-H ).

Elementary analysis (C$_{26}$H$_{45}$NO$_7$S)
Calcd C,60.56;H,8.80;N,2.72;S,6.22
Found C,60.37;H,8.72;N,2.69;S,6.17.

(5) 5- (3,5-Di-tert-butyl-4-hydroxyphenyl ) -4- (N-ethyl-sulfamoyl)-γ-butyrolactone (18)

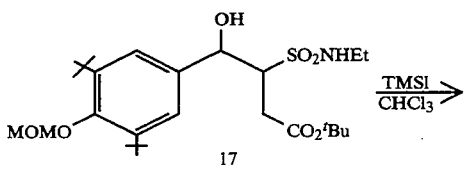

-continued

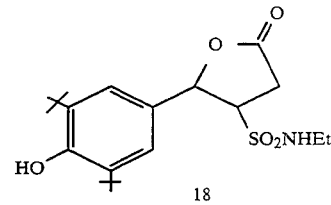

To a solution of tert-butyl 4-(3,5-di-tert-butyl-4-methoxymethoxyphenyl)-4-hydroxy-3-(N-ethylsulfamoyl)butyrate (17) (1.10 g,2.13 mmol) in chloroform (30 ml) was added in one portion iodotrimethylsilane (TMSI) (0.91 ml,6.39 mmol) under icecooling and the resultant solution was stirred for 30 minutes at the same temperature. After the addition of 5% aqueous solution of sodium thiosulfate (70 ml), the reaction mixture was extracted twice with methylene chloride (60 ml). The combined organic layers were washed (×2) with a saturated brine (70 ml), dried over anhydrous sodium sulfate and distilled in vacuo to remove the solvent. The residue, when purified by column chromato10 graphy on silica gel eluting with n-hexane/ethyl acetate (3:1), gave 481 mg (57%) of compound (18) as a colorless solid. M.p. =129°-131° C.

IR(CHCl$_3$)cm$^{-1}$:3626,3374,3288,2960, 1785,1436,1331. p NMR(CDCl$_3$)δ:1.08(3H, t,J=7.2Hz,CH$_3$),1.44(18H, s,2×$^t$Bu), 2.90-3.22(2H, m, CH$_2$), 3.07(2H, d, J=7.6Hz, CH$_2$),3.94(1H, dr, J=5.0, 76Hz. CH),4.25(1H,broad t,J=6.0Hz,NH),5.38(1H, s,OH),5.72(1H,d, J=5.0Hz,CH),7.12(2H,s,2×aromatic-H).

Elementary analysis(C$_{20}$H$_{31}$NO$_5$S)
Calcd C,60.43;H,7.86;N,3.52;S,8.07
Found C,60.32;H,7.84;N,3.55;S,7.85.

(6) (E)-4-(3,5-Di-tert-butyl-4-hydroxyphenyl),3-(N-ethylsulfamoyl)-3-butenoic acid (19)

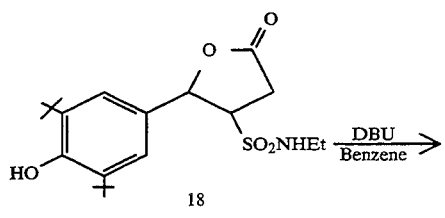

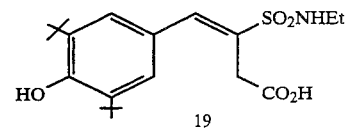

To a solution of 5-(3,5-di-tert-butyl-4-hydroxyphenyl)-4-(N-ethylsulfamoyl)-γ-butyrolactone (18) (1.516 g,3.81 mmol) in benzene (50 ml) was added DBU (1.14 mmol,7.62 mmol) and the mixture was stirred for 30 minutes under the same condition, followed by the addition of 1N HCl (60 ml). The reaction mixture was extracted with ethyl acetate (70 ml). The organic layer was separated, washed with water (60 ml) and a saturated brine (60 ml) and dried over anhydrous sodium sulfate. The solution, when distilled in vacuo to remove the solvent, gave 1.52 g (quant.) of compound 19 as a colorless solid. M.p. =169°–172° C.

IR(KBr)cm$^{-1}$:3604,3267,2958,1719,1631,1596,1430,1326,1158.

NMR(CD3OD)δ:1.15(3H,t,J=7.4Hz,CH₃),1.43(18H, s,2×'Bu), 2.99(2H, q, J=7.4Hz, CH₂),3.63(2H, s, CH₂),7.29(2H, s,2×aromatic-H), 7.58(1H, s,CH).

Elementary analysis(C₂₀H₃₁NO₅S)
Calcd C,60.43;H,7.86;N,3.52;S,8.07
Found C,60.36;H,7.95;N,3.54;S,7.87.

(7) (E)-5- (3,5-Di-tert-butyl-4-hydroxy ) benzylidene-2-ethyl-1, 2-isothiazolidine-3-one-1,1-dioxide (8Ig)

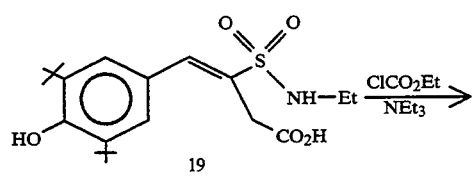

To a solution of (E)-N-ethylaminosulfonyl-4-(3,5-di-tert-butyl-4-hydroxy) phenyl-3-butenoic acid 19 (1.52–3.81 mmol) and triethylamine (0,737 ml,1.5 equivalents) in methylene chloride (60 ml) was added dropwise ethyl chlorocarbonate (0,437 ml,1.2 equivalents) with stirring under cooling with water and the mixture was stirred for another 50 minutes. After water (60 ml) was added, the reaction mixture was extracted with methylene chloride (50 ml). The organic layer was washed with saturated brine (70 ml), dried over anhydrous sulfate and distilled in vacuo to remove the solvent. The resulting crude crystals were washed with ether to give 1.30 g (89.9%) of the objective compound as colorless crystals.

Compound 8Ig: m.p.=188°–190° C.

IR(KBr)cm$^{-1}$:3559, 2960, 11715, 1641, 1598, 1434, 1317, 1159.

NMR(CDCl₃)δ:1.38(3H, t, CH₃),1.46(18H, s,2 ×Bu'), 3.74(2H, q, J=7.2 Hz, CH₂),3.80(2H, d, J=2.4 Hz, CH₂), 5.64(1H, s, OH),7.23(2H, s, Ar-H),7.45(1H, t, J=2.4 Hz, cH).

Elementary analysis(C₂₀H₂₉NO₄S)
Calcd:C,63.30;H,7.70;N,3.69;S,8.45
Found:C,63.07;H,7.71;N,3.72;S,8.30.

Example 37

(E)-5-(3,5-Di-tert-butyl-4-hydroxy)benzylidene-2-ethyl-3-hydroxy-1,22-isothiazolidine-1,1-dioxide (8Ih)

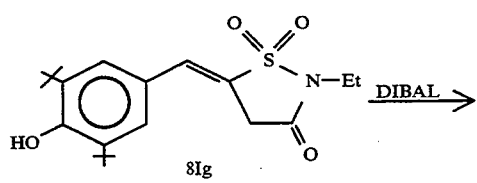

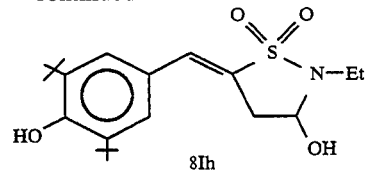

To a solution of compound 8Ig (870 mg,2.29 mmol) in methylene chloride (30 ml) was added dropwise a solution of diisobutylalminium hydride (DIBAL) in hexane (1.0 M, 4.22 ml) with stirring and cooling below −40° C. After about 5 minutes, saturated aqueous solution of ammonium chloride (30 ml) was added to the reaction mixture and the resulting slurry was filtered through celite. To the filtrate was added saturated aqueous solution of ammonium chloride (70 ml) and the mixture was extracted with ethyl acetate (100 ml). The organic layer was washed with a saturated brine (100 ml), dried over anhydrous sodium sulfate and distilled in vacuo to remove the solvent. The resulting crude crystals were recrystallized from a mixture of n-hexane/ether to obtain 762 mg (87.2%) of the objective compound as colorless crystals.

Compound 8Ih: m.p. =138°–141° C.

IR(KBr)cm$^{-1}$:3610, 3427, 2968, 1653, 1595, 1432, 1261, 1214, 1147.

NMR(d₆-acetone)δ:1.27(3H, t, J=7.0 Hz, CH₃),1.48(18H, s,2 ×Bu'),3.01–3.12(1H, m, CH),3.27(2H, q, J=7.0 Hz, CH₂), 3.57(1H, m, CH),5.21–5.24(1H, m, CH(OH)),5.35(1H, broad, OH),7.18(1H, t, J=2.4 Hz, CH),7.37(2H, s, Ar-H).

Elementary analysis(C₂₀H₃₁NO₄S)
Calcd:C,62.96;H,8.19;N,3.67;S,8.40
Found:C,63.05;H,8.26;N,3.67; S,8.33.

Example 38

(E)-5-(3,5-Di-tert-butyl-4-hydroxy)benzylidene-2-ethyl-dihydro-5H-1,2-isothiazole-1,1-dioxide (8Ii)

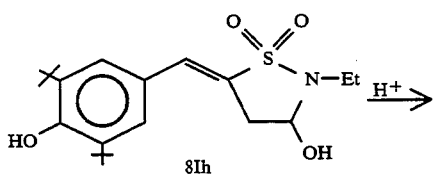

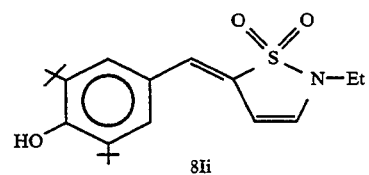

To a solution of compound 8Ih (342 mg,0,896 mmol) in THF (30 ml) was added 2N-hydrochloric acid (one drop). The mixture was stirred for 3 hours at room temperature and saturated aqueous solution of sodium hydrogencarbonate (35 ml) was added. The reaction mixture was extracted with ethyl acetate (30 ml), and the organic layer was washed with saturated brine (35 ml), dried over anhydrous sodium sulfate and distilled in vacuo to remove the solvent. The resulting crude crystals were recrystallized from a mixture of n-hexane:ether to give 296 mg (90.8%) of the objective compound as orange crystals.

Compound 8Ii: m.p. =135°–137° C.

IR(KBr)cm$^{-1}$:3608, 3472, 2961, 1593, 1560, 1435, 1392, 1300, 1212, 1153.

NMR(CDCl$_3$)δ:1.40(3H, t, J=7.2 Hz, CH$_3$),1.43(18H, s,2 ×Bu$^t$),3.52(2H, q, J=7.2 Hz, CH$_2$),5.50(1H, s,OH),6.22(1H, dd, J=0.8, 6.2 Hz, CH),6.54(1H, dd, J=1.8, 6.2 Hz, CH), 6.84(1H, broad, CH),7.30(2H, s, Ar-H).

Elementary analysis(C$_{20}$H$_{29}$NO$_3$S)
Calcd:C,66.08;H,8.04;N,3.85;S,8.82
Found:C,66.53;H,8.08;N,3.82;S,8.68.

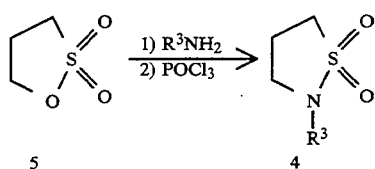

Reference Example 1 (R$^3$ =CH$_2$CH$_2$CH$_3$)

N-n-Propyl-1,2-isothiazolidine-1,1-dioxide (4e)

To γ-sulton (12.2 g,0.1 mol) was added n-propylamine (5.9 g,0.1 mmol) with stirring and ice-cooling. As the reaction proceeds, the contents solidified. To the solid product was added phosphorus oxychloride (10 ml). The reaction mixture was heated to reflux for 2 hours and then distilled in vacuo to remove the remaining phosphorus oxychloride. After the addition of ether (100 ml) to the residue, insoluble substances were removed by filtration. The ether layer was dried over anhydrous sodium sulfate and distilledin vacuo to remove the solvent to give the objective compound 4e (15.2 g,93%) as a colorless oil. This product agreed with the authentic sample obtained in Preparation 5.

Reference Example 2 (R$^3$ =CH$_2$CH(CH$_3$)$_2$)

N-Isobutyl-1,2-isothiazolidine-1,1-dioxide (4c)

According to a similar method as that of Reference example 1, γ-sulton (12.2 g,0.1 mol), isobutylamine (7.3 g,0.1 mol) and phosphorus oxychloride (10 ml) were reacted to give the objective compound 4c (15.9 g,93%). This product agreed with the authentic sample obtained in Preparation 3.

Compounds of the present invention of the formula I as prepared in the above Examples were evaluated in vitro and in vivo experiments for its usefulness as an antiinflammatory drug. E-5110, one of control compounds in the following Experimental Examples, is N-methoxy-3-(3,5-di-t-butyl-4-hydroxybenzylidene)-2-pyrrolidone which is described in Japanese Patent Publication (KOKAI) No. 257967/1986.

Experiment 1

Inhibitory Activity Against the Production of PGE$_2$ in Rat Synovial Membrane Cells Synovial membrane tissues of LEW/Crj male rats (300–350 g weight) were collected and subcultured under a constant condition until the number of cells reached that sufficient for the test. The cultured cells were placed into 96-well plates at 4–10$^3$cells/160 μl/well and incubated in a CO$_2$ incubator for 72 hours. To each well were added a solution (20 μl) containing a various concentration of a drug to be tested and human IL-1β(20 μl) (final concentration: 30 U/ml) simultaneously and the reaction was carried out in a CO$_2$ incubator for 15 hours. The supernatant was preserved at −80° C. until the measurement of PGE$_2$. The measurement of PGE$_2$ was conducted by RIA using $^{125}$I-PGE$_2$ after thawing the preserved samples. The results are shown in Table 1 below.

Experiment 2

Inhibitory Activity Against the Production of LTB4 in Rat Celiac Cells

Jci-SD male rats (300–350 g weight) were injected intraperitoneally with Hanks' solution (10 ml) containing 0.1% bovine serum albumin (BSA) and 25 U/ml heparin. Ascites was collected and centrifuged for 5 minutes at 4° C. at 1500 rpm. The cell fraction (precipitates) was suspended in Hanks' solution containing 0.1% BSA and the cell density was adjusted to 1×10$^6$ cells/ml. The adjusted suspension (800 μl; 8×10$^5$ cells) was transferred to polypropylene tubes and incubated at 37° C. for 10 minutes. After the addition of a solution (100 μl) containing a various concentration of a drug to be tested, the tube was incubated for another 10 minutes, which was followed by the addition of Ca-ionophore A23187 (100 μl; final concentration,1 μM). The reaction was carried out for 15 minutes and then stopped by cooling with ice. The suspension was centrifuged at 4° C. at 3000 rpm for 5 minutes to collect the supernatant, which was preserved at −80° C. until measurement. The measurement of LTB4 was carried out by RIA using $^3$H-LTB$_4$ after thawing the preserved sample. The results are shown in Table 1 below.

Experiment 3

Inhibitory Activity Against the Production of IL-1 under LPS Stimulation in THP-1 Cells THP-1 cells were dispersed in RPMI1640. To each well of 24 well plate were added 800 μl of the dispersion (5×10$^6$ cells/ml),100 μl of a solution containing various concentration of a drug to be tested and 100 μl of LPS (final concentration,10 μg/ml) and the reaction was started. The reaction mixture was allowed to stand for 24 hours at 37° C. The supernatant were collected and centrifuged at 3000 rpm for 10 minutes. The measurement of IL-1 in the supernatant was conducted by RIA using $^{125}$I-IL-1β. The results are shown in Table 1 below.

TABLE 1

Result of In vitro Tests

| Compound No. | $R^3$ | $IC_{50}$ ($\mu$M) PGE$_2$ (Rat SVC) | LTB$_4$ (Rat PEC) | IL-1 (THP-1) |
|---|---|---|---|---|
| 8a | Et | <0.001 | 6.0 | 10 |
| 8b | Me | <0.001 | 2.8 | 21 |
| 8f | OMe | 0.001 | 3.0 | >100 |
| 8g | OCH$_2$H$_6$H$_5$ | 0.18 | 2.5 | 11 |
| 8l | 2-pyridyl | 1.0 | 3.0 | 19 |
| 8w | CONHOH | 0.024 | 6.0 | 20 |
| 8u | CON(OMe)Me | 0.1 | 28 | 100 |
| 10a | H | 0.03 | >100 | >100 |
| 11a | OH | 0.013 | 9.5 | 90 |
| 8b | Me | <0.001 | 1.8 | 29 |
| 8f | OMe | <0.001 | 1.5 | — |
| 8l | 2-pyridyl | >1 | 1.4 | 100 |
| 11b | OH | 0.012 | 9.6 | 90 |
| E-5110 | | 0.005 | 6.0 | >100 |
| Indomethacin | | 0.002 | >100 | >100 |

(Structures: t-Bu/HO/t-Bu-substituted phenyl linked via vinyl to a cyclic sulfonamide with $R^3$ substituent.)

Experiment 4

Suppressive Activity Against Carrageenin-induced Edema in Rats

The experiment was carried out in accordance with the Winter's method (Winter, C.A. et. al., Proc. Soc. Exp. Biol. Med., vol.111: 54 (1962)) with a modification. Namely, LEW/Crj male rats (6 weeks of age,140–170 g weight) which had been fasted for 24 hours were divided into groups each consisting of 7 to 8 rats. One hour after the administration of a drug, each animal was injected subcutaneously with 0.1 ml of 1%$\lambda$-carrageenin (PICININ-A, Zushikagaku) solution at plantar of right hind leg to cause edema. The volume of the right hind leg was measured with a volume measuring instrument by the water displacement method before the injection and every 1 hour for 5 hours after the injection. The effect of a drug was evaluated by calculating the edema suppression rate in drug-administered group relative to vehicle-administrated group according to the Dunnett-t test. The anti-edema effect of a drug was expressed as ED$_{50}$ (mg/kg) which was obtained by regression analysis on the basis of the suppression rate at 3 or 4 hours after carrageenin administration. The results are shown in Table 2 below.

Experiment 5

Inhibitory Effect of Lesion Formation of Gastric Mucosa in Rats

LEW/Crj male rats (6 weeks of age,140–160 g weight) were divided in groups of 6 rats on the basis of dose of a drug to be tested. A drug was administered to animals which had been fasted for 24 hours prior to the test and, six hours later, animals were anesthetized with ether and killed by exsanguination. The gaster was extracted and physiological saline (about 6 ml) was included in it. Subsequently, the gaster was dipped in 15% formalin solution for about 15 minutes and cut out along its greater curvature. The state of the disorder of the gaster was observed with a stereoscopic microscope, and the number of rats showing the gaster disorder and the length of bleeding plaques were determined. The extent of disorder was expressed by Lesion Index (mm) which is a cumulative value of length of bleeding plaques of each group of drug-administrated groups. The strength of the effect of drugs was expressed as UD$_{50}$ (mg/kg) calculated by Probit method on the basis of the number of cases showing disorder in a group to which a given dose of a drug was administered. Results are shown in Table 2 below.

TABLE 2

Results of In Vivo Test

| | Compound No. | $R^3$ | Edema (Rat carrageenin) (ED$_{50}$) |
|---|---|---|---|
| | 8a | Et | 1.7 |
| Control compound | E-5110 | | 3 |
| | Indomethacin | | 0.8 |

Inhibitory effect of lesion formation of gastoric mucosa in rats

| Compd. No. | $R^3$ | Dose, (po) mg/kg | No. of cases | Number wherein disorder occurred | UD$_{50}$, mg/kg | Lesion Index (mm) |
|---|---|---|---|---|---|---|
| 8a | Et | 3 | 7 | 0 | >400 | 0.00 ± 0.00 |
| | | 10 | 7 | 1 | | 0.04 ± 0.04 |
| | | 30 | 7 | 0 | | 0.00 ± 0.00 |
| | | 100 | 7 | 1 | | 0.17 ± 0.17 |

TABLE 2-continued

| Results of In Vivo Test | | | | | | |
|---|---|---|---|---|---|---|
| | | 400 | 7 | 1 | | 0.03 ± 0.03 |
| Control | E-5110 | 0.3 | 6 | 0 | 1 | 0 ± 0 |
| compound | | 1 | 6 | 4 | | 0.58 ± 0.32 |
| | | 3 | 6 | 6 | | 4.52 ± 1.31 |
| | | 10 | 12 | 12 | | 4.0 ± 1.14 |
| | | 30 | 12 | 12 | | 6.47 ± 1.77 |
| | | 100 | 12 | 12 | | 11.6 ± 2.44 |
| | Indomethacin | 1 | 6 | 0 | 3 | 0 ± 0 |
| | | 3 | 6 | 3 | | 1.83 ± 0.95 |
| | | 10 | 24 | 24 | | 8.15 ± 1.5 |
| | | 30 | 24 | 24 | | 19.5 ± 2.1 |

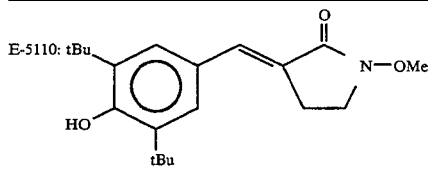

As is apparent from the results of experiments, the compounds of the present invention have an activity to suppress the production of PGE$_2$, LTB$_4$, IL-1 and the like without serious side effects on gastric mucosa and are expected to be useful as an active ingredient for medical formulations for the treatment of inflammatory diseases.

| Medical formulations | |
|---|---|
| Granules | |
| Compound 8a | 20 mg |
| Lactose | 250 mg |
| Corn starch | 115 mg |
| Hydroxypropylcellulose | 115 mg |

Above materials are granulated in a conventional wet method to obtain granules.

What is claimed is:

1. A compound of the formula

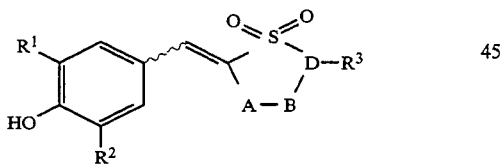

wherein A is -CH$_2$- or -CH$_2$CH$_2$-;

B is -CH$_2$-, -CHOH-, -CO-, -O-, or A and B taken together may form -CH=CH-;

D is >N- or >CH-;

R$^1$ and R$^2$ each independently is hydrogen, C$_1$-C$_8$- alkyl or C$_1$-C$_6$alkoxy;

R$^3$ is (1) hydrogen,
(2) C$_1$-C$_8$ alkyl,
(3) C$_3$-C$_7$ cycloalkyl,
(4) C$_1$-C$_6$alkoxy,
(5) aryl-substituted C$_1$-C$_6$ alkoxy wherein aryl is phenyl or naphthyl which groups are unsubstituted or are substituted with halogen, C$_1$-C$_6$ alkoxy, C$_1$-C$_8$ alkyl or nitro,
(6) heteroaryl-substituted C$_1$-C$_6$ alkoxy wherein heteroaryl is a cyclic group containing 1-4 hetero atoms,
(7) acetyl,
(8) propionyl,
(9) butyryl.
(10) valeroyl,
(11) hexanoyl,
(12) heptanoyl,
(13) octanoyl,
(14) benzoyl,
(15) 4-chlorobenzoyl,
(16) 4-methoxybenzoyl,
(17) 4-nitrobenzoyl,
(18) 3,4-dichlorobenzoyl,
(19) 3,4-dimethoxybenzoyl,
(20) 3,4-dinitrobenzoyl,
(21) 1-naphthoyl,
(22) 2-naphthoyl, or
(23) carbamoyl which is unsubstituted or is substituted at the nitrogen atom by one or more substituents selected from the group consisting of
 (a) C$_1$-C$_8$ alkyl,
 (b) C$_1$-C$_6$ alkoxy,
 (c) hydroxy,
 (d) C$_3$-C$_7$ cycloalkyl,
 (e) aryl-substituted C$_1$-C$_8$ alkyl wherein aryl is phenyl or naphthyl which groups are unsubstituted or are substituted with halogen, C$_1$-C$_6$ alkoxy, C$_1$-C$_8$ alkyl or nitro,
 (f) C$_1$-C$_6$ alkoxy-substituted C$_1$-C$_8$ alkyl,
 (g) C$_2$-C$_9$ alkylcarbonyl,
 (h) benzoyl,
 (i) 4-chlorobenzoyl,
 (j) 4-methoxybenzoyl,
 (k) 4-nitrobenzoyl,
 (l) 3,4-dichlorobenzoyl,
 (m) 3,4-dimethoxybenzoyl,
 (n) 3,4-dinitrobenzoyl,
 (o) 1-naphthoyl,
 (p) 2-naphthoyl,
 (q) C$_3$-C$_7$ cycloalkyloxy, and
(r) aryl-substituted C$_1$-C$_6$ alkyloxy wherein aryl is phenyl or naphthyl which groups are unsubstituted or are substituted with halogen, C$_1$-C$_6$ alkoxy, C$_1$-C$_8$ alkyl or nitro;

or R$^3$ represents a group of the formula

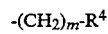

-(CH$_2$)$_m$-R$^4$ wherein $R^4$ is
(1) hydrogen,
(2) hydroxy,
(3) mono- or di-substituted amino wherein the substituent is selected from the group consisting of (a) $C_1$-$C_8$ alkyl and (b) aryl-substituted $C_1$-$C_8$ alkyl wherein aryl is phenyl or naphthyl which groups are unsubstituted or are substituted with halogen, $C_1$-$C_6$ alkoxy, $C_1$-$C_8$ alkyl or nitro,
(4) phenyl or naphthyl which groups are unsubstituted or are substituted with halogen, $C_1$-$C_6$ alkoxy, $C_1$-$C_8$ alkyl or nitro,
(5) a cyclic group containing 1–4 hetero atoms,
(6) hydroxycarbonyl,
(7) methoxycarbonyl,
(8) ethoxycarbonyl,
(9) propoxycarbonyl,
(10) isopropoxycarbonyl,
(11) butoxycarbonyl,
(12) isobutoxycarbonyl, or
(13) tert-butoxycarbonyl;
and n is an integer of 0–3.

2. A compound as claimed in claim 1 wherein $R^1$ and $R^2$ each are tert-butyl.

3. A compound as claimed in claim 1 or claim 2 wherein A is -$CH_2$-; B is -$CH_2$- and D is >N-.

4. A compound as claimed in any one of claims 1 or 2, wherein $R_3$ is $C_1$-$C_8$ alkyl or $C_3$-$C_7$ cycloalkyl.

5. A compound as claimed in claim 3 wherein $R_3$ is $C_1$-$C_8$ alkyl or $C_3$-$C_7$ cycloalkyl.

6. An anti-inflammatory composition which comprises an anti-inflammatory effective amount of a compound according to claim 1 as an active ingredient and a pharmaceutically acceptable carrier therefor.

* * * * *